(12) United States Patent
Misra et al.

(10) Patent No.: US 7,105,725 B2
(45) Date of Patent: Sep. 12, 2006

(54) PATHOGEN RESISTANT TRANSGENIC PLANTS EXPRESSING CEMA OR CEMA-RELATED PEPTIDES

(75) Inventors: Santosh Misra, Victoria (CA); William W. Kay, Victoria (CA); Milan Osusky, Victoria (CA)

(73) Assignee: University of Victoria Innovation and Development Corporation, Victoria (CA)

( * ) Notice: Subject to any disclaimer, the term of this patent is extended or adjusted under 35 U.S.C. 154(b) by 0 days.

(21) Appl. No.: 10/421,635

(22) Filed: Apr. 21, 2003

(65) Prior Publication Data

US 2004/0064847 A1 Apr. 1, 2004

Related U.S. Application Data

(63) Continuation of application No. 09/616,110, filed on Jul. 14, 2000, now abandoned.

(60) Provisional application No. 60/165,249, filed on Nov. 12, 1999.

(51) Int. Cl.
- A01H 5/00 (2006.01)
- C12N 15/82 (2006.01)
- C12P 21/02 (2006.01)

(52) U.S. Cl. ............... 800/301; 800/279; 530/344
(58) Field of Classification Search ............... None
See application file for complete search history.

(56) References Cited

U.S. PATENT DOCUMENTS 5,631,007 A  5/1997  Ryals et al.
5,707,855 A * 1/1998  Hancock et al. ....... 435/252.33

FOREIGN PATENT DOCUMENTS

WO  WO 94/04688  3/1994
WO  WO 95/16776  6/1995

OTHER PUBLICATIONS

Guo et al, 2004. Proc. Natl. Acad. Sci. USA 101: 9205-9210.*
Hancock et al., "Cationic Peptides: A New Source of Antibiotics," *TIBTECH* 16:82-88 (1998).
Hassan et al., "Transformation of Potato (*Solanum tuberosum*) with a Gene for an Anti-Bacterial Protein, Cecropin," *Acta Hort.* 336:127-131 (1993).
Hill et al., "Functional Analysis of Conserved Histidines in ADP-Glucose Pyrophosphrylase from *Escherichia coli*," *Biochem. Biophys. Res. Comm.* 244:573-577 (1998).
Huang et al., "Expression of an Engineered Cecropin Gene Cassette in Transgenic Tobacco Plants Confers Disease Resistance to *Pseudomonas syringae* pv. *tabaci*," *Phytopathology* 87:494-499 (1997).
Osusky et al., "Transgenic Plants Expressing Cationic Peptide Chimeras Exhibit Broad-Spectrum Resistance to Phytopathogens," *Nature Biotechnol.* 18:1162-1166 (2000).
Lazar et al., "Transforming Growth Factor α: Mutation of Aspartic Acid 47 and Leucine 48 Results in Different Biological Activities," *Mol. Cell. Biol.* 8:1247-1252 (1988).

* cited by examiner

*Primary Examiner*—Anne Kubelik
(74) *Attorney, Agent, or Firm*—Klarquist Sparkman, LLP

(57) ABSTRACT

Transgenic plants that express antimicrobial CEMA and/or CEMA-related peptides are disclosed. In certain embodiments, these plants have enhanced, broad-spectrum pathogen resistance and are useful as agricultural or horticultural crops. In other embodiments, the plants are used to produce large quantities of the CEMA and/or CEMA-related peptides.

55 Claims, 7 Drawing Sheets

CEMA:    KWKLFKKIGIGAVLKVLTTGLPALKLTK
ECEMA:   MALEHMKWKLFKKIGIGAVLKVLTTGLPALKLTK

Fig. 2A
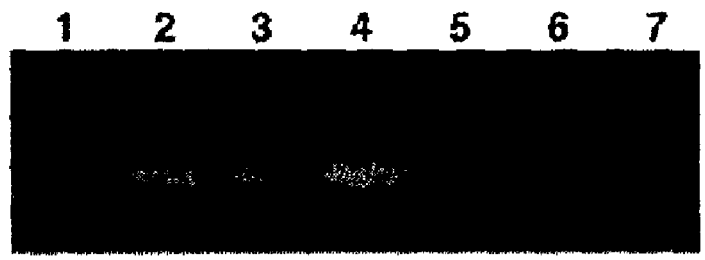
Fig. 2B
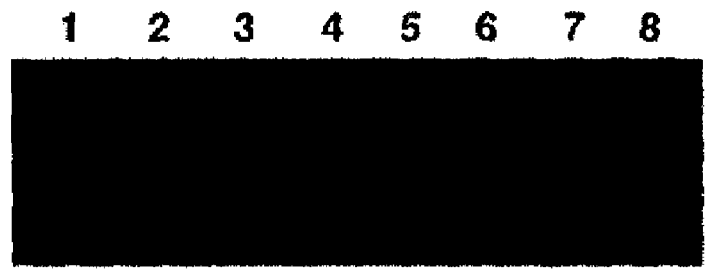
Fig. 2C
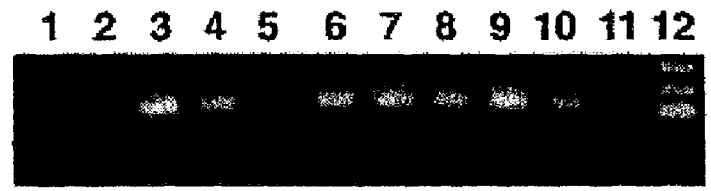
Fig. 2D
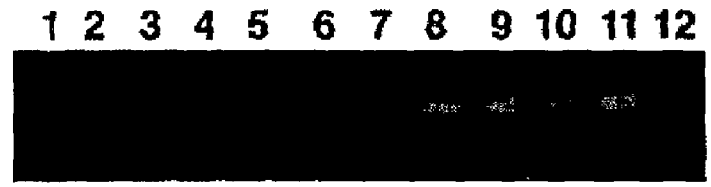
Figs. 2A-2D Fig. 4A
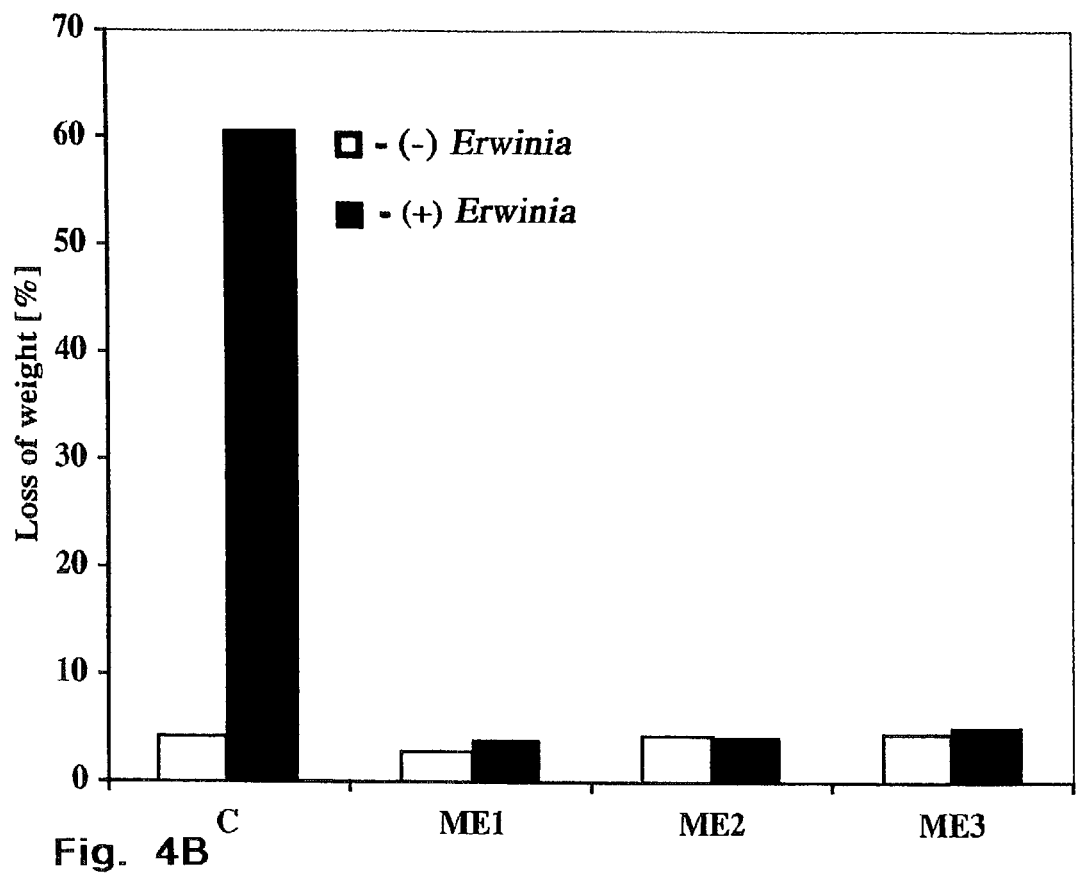
Fig. 4B
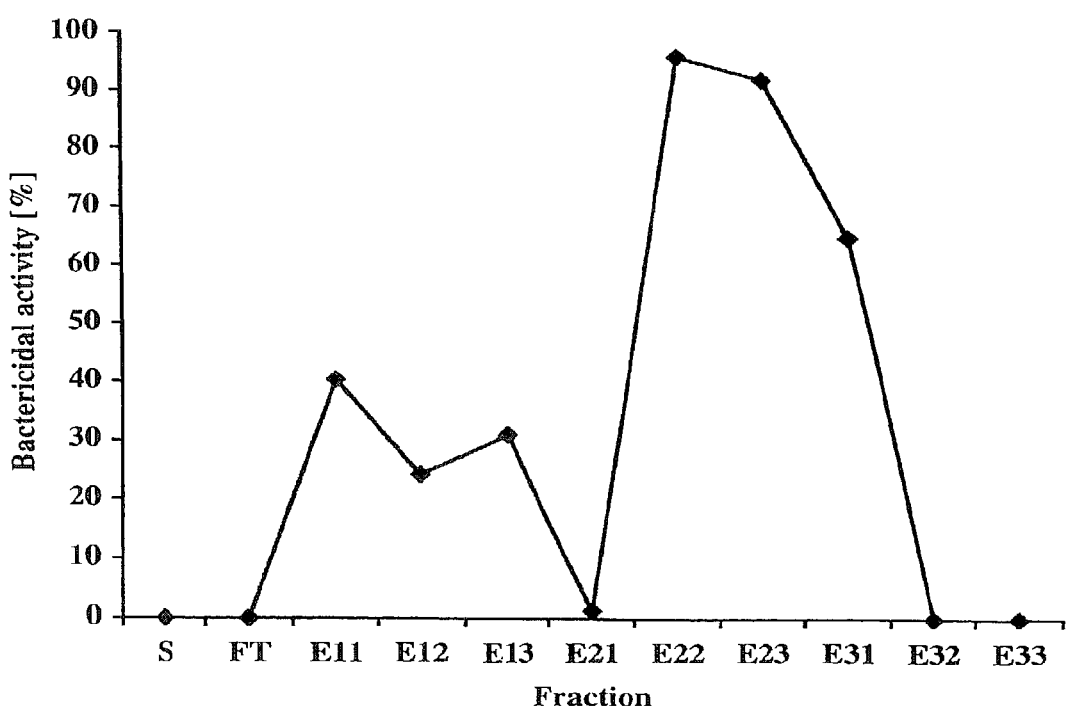
Figs. 4A and 4B

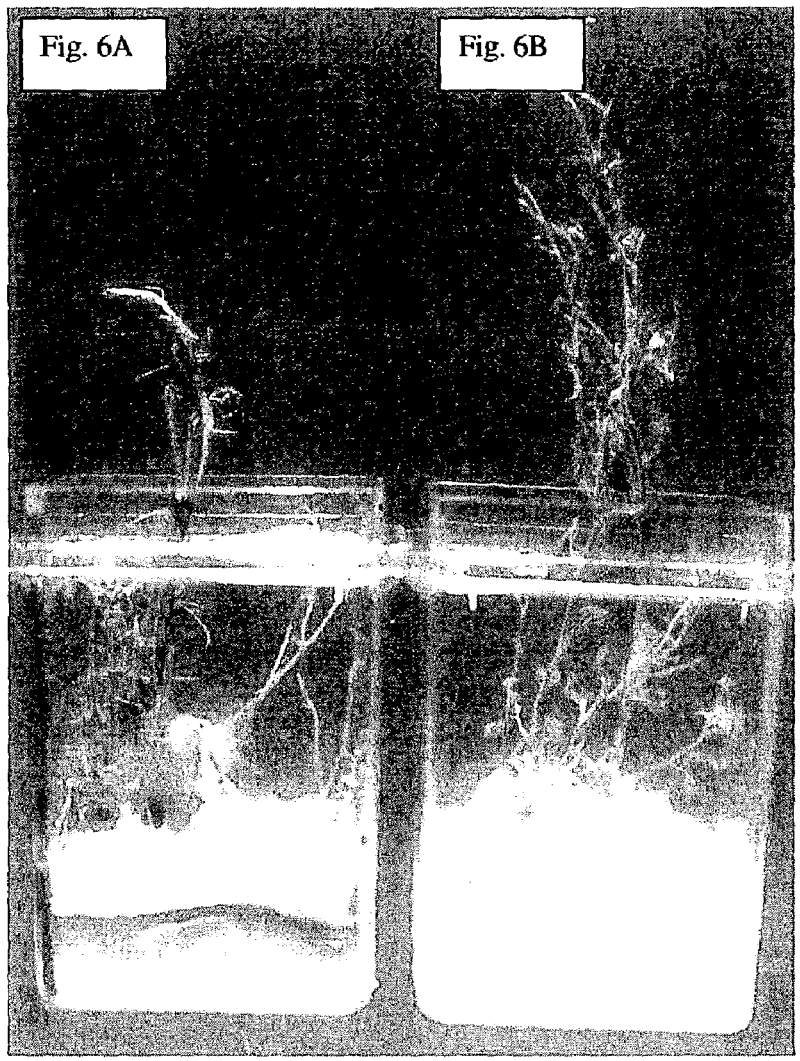
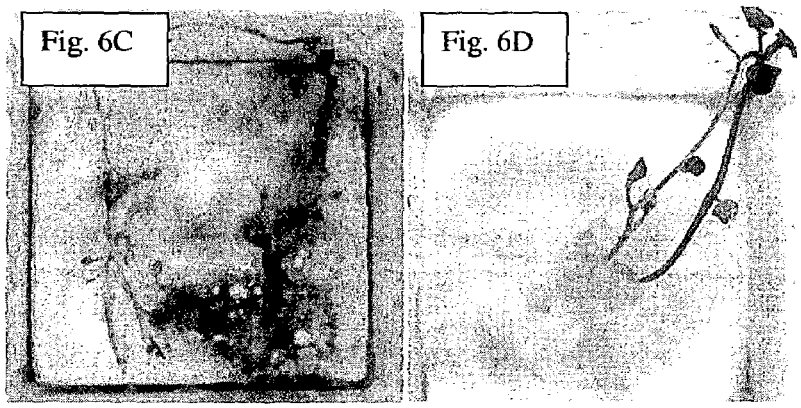
Figs. 6A-6D

SEQUENCE LISTING

```
<160> NUMBER OF SEQ ID NOS: 11

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence: Engineered
      DNA sequence encoding a  cationic peptide

<400> SEQUENCE: 1
aaatggaaac tgttcaagaa gatcggcatc ggcgccgtgc tgaaactgct gaccaccggt     60
ctgccggcgc tgaagctaac taactaa                                         87

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Engineered
      Cationic Peptide
```

```
<400> SEQUENCE: 2

Lys Trp Lys Leu Phe Lys Lys Ile Gly Ile Gly Ala Val Leu Lys Val
  1               5                  10                  15

Leu Thr Thr Gly Leu Pro Ala Leu Lys Leu Thr Lys
             20                  25

<210> SEQ ID NO 3
<211> LENGTH: 105
<212> TYPE: DNA
<213> ORGANISM: Artificial Sequence
<220> FEATURE:
<223> OTHER INFORMATION: Description of Artificial Sequence: Nucleic
      acid sequence encoding ECEMA

<400> SEQUENCE: 3
atggctctag agcatatgaa atggaaactg ttcaagaaga tcggcatcgg cgccgtgctg      60
aaagtgctga ccaccggtct gccggcgctg aagctaacta agtaa                     105

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Engineered
      Cationic Peptide

<400> SEQUENCE: 4

Met Ala Leu Glu His Met Lys Trp Lys Leu Phe Lys Lys Ile Gly Ile
  1               5                  10                  15

Gly Ala Val Leu Lys Val Leu Thr Thr Gly Leu Pro Ala Leu Lys Leu
             20                  25                  30

Thr Lys

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: N-terminal
      extension

<400> SEQUENCE: 5

Ala Met Trp Lys
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: N-terminal
      extension

<400> SEQUENCE: 6

Ala Ser Arg His
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: N-terminal
      extension
```

```
<400> SEQUENCE: 7

Ala Leu Trp Lys
 1

<210> SEQ ID NO 8
<211> LENGTH: 24
<212> TYPE: PRT
<213> ORGANISM: Rana temporaria

<400> SEQUENCE: 8

Glu Glu Glu Arg Asn Ala Glu Glu Arg Arg Asp Glu Pro Asp Glu
 1               5                  10                  15

Arg Asp Val Gln Val Glu Lys Arg
            20

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: PCR
      primer

<400> SEQUENCE: 9
caaggaaaaa cggtctagag catatgaaat ggaaac                           36

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 10
gaactcgagc agcgagctct tacttagtta gcttc                            35

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: N-terminal
      extension

<400> SEQUENCE: 11

Met Ala Leu Glu His Met
 1               5
```

PATHOGEN RESISTANT TRANSGENIC PLANTS EXPRESSING CEMA OR CEMA-RELATED PEPTIDES

CROSS-REFERENCE TO RELATED APPLICATIONS

This application is a continuation of U.S. patent application Ser. No. 09/616,110, filed Jul. 14, 2000, now abandoned which claims the benefit of provisional application No. 60/165,249, filed Nov. 12, 1999, both of which are herein incorporated by reference.

FIELD OF THE INVENTION

This invention relates to plants that are genetically engineered to express one or more peptides belonging to the cecropin-mellitin hybrid families.

BACKGROUND OF THE INVENTION

Disease in Plants

Plants are hosts to any of various infectious diseases (numbering in the thousands) caused by a vast array of respective phytopathogenic fungi, bacteria, viruses, and nematodes, for example, these pathogens are responsible for significant crop losses worldwide, resulting from both infection of growing plants and destruction of harvested crops. The most widely practiced methods of reducing damage caused by such pathogens involve the use of various chemical agents that kill or attenuate the action of the respective pathogen. Unfortunately, many plant pathogens develop resistance to such chemicals, and some plant pathogens (especially viruses) are not susceptible to control by chemical means. In addition, many of the chemical agents used are broad-spectrum toxins, and may cause serious environmental damage, as well as toxicity in humans and animals.

Plant breeding and, more recently, genetic engineering techniques also have been employed to combat plant pathogens. In certain instances, breeders and molecular biologists have successfully engineered resistance in plants to certain pathogens. In the past few years, a number of plant R (resistance) genes have been isolated from plants. When introduced into otherwise susceptible crops, these R genes produce enhanced resistance to certain pathogens. For example, U.S. Pat. No. 5,571,706 describes the isolation of the tobacco N gene that confers enhanced resistance to Tobacco Mosaic Virus. However, whereas conventional breeding and genetic engineering approaches reported to date can successfully enhance pathogen resistance in plants, the approaches typically address problems caused by only one target pathogen, or a small number of closely related pathogens. As a result, while crops produced using these approaches may have enhanced protection against the target pathogen, conventional chemical agents still must be used to control other pathogens.

Antimicrobial Peptides

In the past two decades a large number of natural polypeptides ("peptides") with a broad range of antimicrobial activities have been discovered (for reviews see Hancock and Lehrer, *Trends Biotechnol.* 16:22–28, 1998; Hancock, *Mol. Microbiol.* 12:951–958, 1994; and Nicholas and Mor, *Ann. Rev. Microbiol.* 49:277–304, 1995). The endogenous antimicrobial peptides of plants and animals typically consist of 12–45 amino acids, and are amphipathic molecules having a net positive charge (cationic) at physiological pH.

Although cationic antimicrobial peptides (CAPs) are structurally diverse, they fall into two general classes of structures: α-helical peptides, such as the cecropins and magainans, and β-sheet peptides stabilized by intramolecular disulphide bonds, such as the defensins, protegrins, and tachyplesins. Hancock and Lehrer, *Trends Biotechnol.* 16: 22–28, 1998; Zasloff, *Curr. Opin. Immunol.* 4:3–7, 1992; Cociancich et al., *Biochem. J.* 300:567–575 1994; and Piers and Hancock, *Mol. Microbiol.* 12:951–958, 1994. Natural CAPs vary greatly in their respective spectra of biological activities, including killing bacteria (Gram-positive and -negative), fungi, protozoa, and even viruses. CAPs normally kill susceptible microorganisms in vitro at concentrations from 0.25 µg/mL to 4 µg/mL (Hancock and Lehrer, *Trends Biotechnol.* 16: 22–28, 1998), providing exciting possibilities in the face of the declining efficiency of conventional antibiotics. Furthermore, the expression of CAP in plants may introduce broad-spectrum resistance to phytopathogenic microorganisms. Jaynes, *Plant Science* 89:43–53, 1993; and Misra and Zhang, *Plant Physiol.* 106: 977–981, 1994.

Insect cecropins represent a family of small, highly basic, α-helical antimicrobial peptides that form an important component in the immune response of insects. Bohman and Hultmark, *Annu. Rev. Microbiol.* 41:103–126, 1987. Cecropins isolated from the giant silk moth, *Hyalophora cecropia*, contain about 35 amino acid residues with amphipathic N-termini and hydrophobic C-termini (van Hofsten et al., *Proc. Natl. Acad. Sci. USA* 82:2240–2243, 1985). All cecropins are potent antibacterials in vitro, and several members of this family are particularly powerful in vitro against a number of plant pathogenic bacteria. Hultmark et al., *Eur. J. Biochem.* 127:207–217, 1982; Jaynes et al., *BioEssays* 6:263–270, 1987; and Nordeen et al., *Plant Sci.* 82:101–107, 1992.

Another antibacterial peptide, mellitin, containing 26 amino acids, is the major component of bee venom. As opposed to cecropins, mellitin has a predominantly hydrophobic N-terminus with an amphipathic C-terminus. Habermann, *Science* 177:314–322, 1972. Although mellitin possesses potent antimicrobial activity, its powerful hemolytic activity (Tosteson et al., *J. Membr. Biol.* 87:35–44, 1985) makes it unsuitable for therapeutic use and likely a poor candidate for transgenics.

In view of the above, there is a need for plants having enhanced resistance to a wider than normal spectrum of pathogens, including bacterial and fungal pathogens.

SUMMARY OF THE INVENTION

The present inventors have discovered that the expression of certain cationic antimicrobial peptides (CAPs) in transgenic plants confers resistance to a wider than normal spectrum of pathogens, including enhanced resistance to both fungal and bacterial pathogens. Furthermore, the inventors have discovered that such CAPs can be modified through the addition of amino acid residues on either the N-terminus or the C-terminus (terminal extensions) so as to render the CAPs more compatible with plant physiology. The subject CAPs are related to small, positively charged (cationic) peptides belonging to the cecropin-mellitin (CEMA) hybrid families, which contain parts of the naturally occurring peptides cecropin A and mellitin. Piers and Hancock, *Mol. Microbiol.* 12:951–958, 1994; and Hancock and Lehrer, *Trends Biotechnol.* 16:22–28, 1998.

Transgenic plants according to the invention may be used in conventional agricultural applications, such as food crops.

Alternatively, the plants may be harvested and processed to extract the expressed CEMA, or a CEMA-related peptide such as ECEMA, described below. In these ways the isolated peptides can be used for medicinal purposes. In addition, the plants may be either used directly or indirectly as a feed-additive medicinal plant to combat microbial infections in animals, such as humans.

The invention, thus, encompasses transgenic plants that express at least one CEMA and/or at least one CEMA-related peptide, and methods for producing such plants. Parts of such plants, including seeds, fruits, stems, leaves, and roots, may be utilized conventionally as food sources, or as sources of the CEMA and/or CEMA-related peptides. Because all plant types are susceptible to one or more plant pathogens, the present invention may be used for producing broad-spectrum resistance in any of various plant types. Thus, the invention may be applied to both monocotyledonous, dicotyledonous, and gymnospermous plants, including, but not limited to, maize, wheat, rice, barley, soybean, cotton, legumes, rape/canola, alfalfa, flax, sunflower, safflower, brassica, cotton, flax, peanut, and clover; vegetables such as lettuce, tomato, cucurbits, cassava, potato, carrot, radish, pea, lentil, cabbage, cauliflower, broccoli, Brussels sprouts, and peppers; tree fruits such as citrus, apples, pears, peaches, apricots, and walnuts; and flowers such as orchids, carnations, and roses; coffee; cacao; conifers such as Douglas fir, spruce, and pine; and woody deciduous trees such as poplar and elms.

One aspect of the invention provides transgenic plants that express one or more CEMA peptides and/or one or more CEMA-related peptides. Examples of CEMA peptides that may be used include, but are not limited to, the CEMA peptides described by Hancock et al., U.S. Pat. No. 5,707, 855.

Another aspect of the invention provides CEMA-related peptides that are modified to contain additional amino acids, thereby forming "fusion" peptides. Expression of fusion peptides in transgenic plants may provide even more effective broad-spectrum pathogen resistance than expression of CEMA in such plants, or may enhance the stability of the expressed CEMA-related peptides to provide higher expression levels. Thus, purification of the peptide from plant tissues is enhanced. In other embodiments, the invention provides transgenic plants that express a fusion peptide comprising:

(1) a first peptide sequence that is a CEMA-related peptide; and (2) a second peptide sequence operably linked to the first peptide sequence.

The second peptide sequence is typically, but not necessarily, linked to the amino (N-) terminus of the first peptide sequence.

In certain embodiments, the second peptide sequence comprises an anionic (negatively charged) "pro-region" peptide sequence. Such pro-region sequences serve to neutralize the cationic nature of the CEMA or CEMA-related peptide(s) and may thus provide enhanced stability in cellular environments or a decrease in the toxicity of the CEMA or CEMA-related peptide to the host organism. Thus, pro-regions generally include a number of negatively charged amino acids, such as glutamate (Glu or E) and aspartate (Asp or D). For example, suitable pro-regions are usually found in naturally occurring unprocessed (full-length) dermaseptin and temporin peptides. Anionic pro-regions can be obtained from other peptides, including peptides of mammalian origin, such as the pro-region from a sheep cathelin protein. Fusion peptides that include such pro-regions may be represented as P-C.

Pro-region peptides may be joined directly to the N-terminus of a CEMA or CEMA-related peptide. However, the pro-region and the cationic peptides also can be joined using a spacer peptide. The use of spacer peptides to join two peptide domains is well known in the art. Suitable spacer peptides are typically 2 to 25 amino acids long, and provide a flexible hinge connecting the first peptide sequence to the second peptide sequence. Spacer sequences that have been used to provide flexible hinges connecting two peptide sequences include the glycine(4)-serine spacer (GGGGS x3: SEQ ID NO: 12) described by Chaudhary et al., *Nature* 339:394–397, 1989.

The invention also provides for CEMA-related peptides containing N-terminal extensions. One such peptide is ECEMA (SEQ ID NO: 4). Such N-terminal extensions can serve to decrease or increase the anti-microbial effect of the CEMA-peptide, and, therefore, make the peptide more compatible with plant physiology (meaning that the plant can grow and thrive in a manner comparable to its non-transgenic counterpart). The N-terminal extension may serve to provide the spacer-peptide function. Fusion peptides that comprise a pro-region peptide, a spacer peptide, and a CEMA peptide are represented as P-S-C, wherein S represents the spacer peptide.

Spacer sequences may also include a cleavage site, such as a peptide sequence recognized and cleaved by a protease. Cleavage sites facilitate removal of the pro-region from the CEMA peptide following purification of the CEMA peptide from plant tissues.

Finally, the invention also provides plants that have increased shelf-life and storage life. The increase in shelf-life can be observed by comparing the trangenic plants of the invention to control non-transformed plants. Increased shelf-life is especially desirable for long term storage of fruits and vegetables, for preserving cut flowers, and for preserving medicinal plants. These and other aspects of the invention are described in further detail below.

SEQUENCE LISTING

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 is the nucleic acid sequence encoding CEMA.

SEQ ID NO: 2 is the amino acid sequence of the CEMA peptide.

SEQ ID NO: 3 is the nucleic acid sequence encoding the ECEMA peptide.

SEQ ID NO: 4 is the representative amino acid sequence of the ECEMA peptide.

SEQ ID NOS: 5–7 are respective amino acid sequences of various N-terminal extension sequences.

SEQ ID NO: 8 is the amino acid sequence of the pro-region of temporin G.

SEQ ID NOS: 9 and 10 are respective PCR nucleotide primers used to amplify the ECEMA-coding sequence.

SEQ ID NOS: 11 is the N-terminal extension sequence used in the ECEMA peptide.

SEQ ID NO: 12 is an exemplary spacer amino acid sequence.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1A shows the amino acid sequence of the cationic peptides CEMA (SEQ ID NO: 2) and the N-terminally extended version, ECEMA (SEQ ID NO: 4). FIG. 1B shows the pSAI4 plasmid expression vector for ECEMA. The abbreviations in the figure are as follows: RB, the right, and LB, the left border regions of the Ti plasmid; NOS-pro, the promoter, and NOS-ter, the terminator of the nopaline synthase gene; NPT II, neomycin phosphotransferase II; 2x35S, duplicated-enhancer CaMV 35S promoter; AMV, leader sequence from alfalfa mosaic virus RNA4; ECEMA, protein-coding sequence of ECEMA.

FIGS. 2A–2D include digital images of respective gels showing ECEMA gene integration and mRNA expression. FIG. 2A shows the results from PCR amplification of total genomic DNA isolated from control (non-transformed) and transgenic Russet Burbank potato plants. The primers for PCR were the same as used in pSAI4 construction. Lane 1, PCR product from plasmid pSAI4 (positive control); lanes 2–4, PCR products from genomic DNA isolated from Russet Burbank transformed with pSAI4; lane 5, PCR product from genomic DNA isolated from control Russet Burbank; lane 6, no template in PCR (negative control); lane 7, molecular size standards (φX174 RF DNA/HaeIII). FIG. 2B shows a digital image of a gel containing ECEMA mRNA expression that was tested by RT-PCR from total RNA isolated from control and transgenic Russet Burbank. The primers for PCR were the same as used in pSAI4 construction. Lane 1, PCR product from RNA isolated from control Russet Burbank, without reverse transcription; lanes 2–4, PCR products from RNA isolated from transgenic Russet Burbank, without reverse transcription (quality control); lane 5, RT-PCR product from control Russet Burbank; lanes 6–8, RT-PCR products from transgenic Russet Burbank. FIG. 2C shows a digital image of the PCR-amplified ECEMA coding sequence that was amplified from total genomic DNA isolated from control (non-transformed) and transgenic Desiree potato plants. The primers for PCR were the same as used in pSAI4 construction. Lane 1, no template in PCR (negative control); lane 2, PCR product from genomic DNA isolated from non-transformed Desiree; lane 3, PCR product from plasmid pSAI4 (positive control); lanes 4–11, PCR products from genomic DNA isolated from Desiree transformed with pSAI4; lane 12, 100-bp ladder (Pharmacia)—bands represent 100, 200, 300 bp. FIG. 2D shows a digital image of the results from ECEMA mRNA expression tests. These tests were conducted using RT-PCR from total RNA isolated from control and transgenic Desiree. The primers for PCR were the same as used in pSAI4 construction. Lane 1, PCR product from RNA isolated from control Desiree, without reverse transcription; lanes 2–5, PCR products from RNA isolated from transgenic Desiree, without reverse transcription (quality control); lanes 6, RT-PCR product from control Desiree; lanes 7–10, RT-PCR products from transgenic Desiree; lane 11, PCR product from plasmid pSAI4 (positive control); lane 12, 100-bp ladder (Pharmacia)—bands represent 100, 200, and 300 bp.

FIGS. 4A and 4B include graphs showing the resistance of transgenic potatoes to *Erwinia carotovora*. FIG. 4A is a graph of results from a soft-rot-resistance study of ECEMA-expressing transgenic Desiree potato tubers. Discs prepared from tubers of control (C) and transgenic plants ME1, ME2, and ME3 were infected with *E. carotovora*. After 6 days at room temperature, rotted tissue was gently removed from the discs and the sensitivity/resistance to *E. carotovora* was expressed as the loss of weight of tuber tissue. FIG. 4B is a graph depicting the bactericidal effect of fractions from ion-exchange chromatography on *E. carotovora*. The protein-isolation technique is described below. S: filtered supernatant applied to the column; FT: flow-through; E11–E13: fractions obtained by elution with 0.2 M NaCl; E21–E23: fractions obtained by elution with 0.3 M NaCl; E31–E33: fractions obtained by elution with 0.5 M NaCl. Protein from the various fractions were separated on Tricine-SDS-polyacrylamide gel and silver stained. Fractions E22, E23, and E31 contained bands that migrated to the same relative location in the gel as the control (the control was 200 ng of chemically synthesized ECEMA protein (3.8 kDa)). As expected, fractions E22, E23, and E31 showed the highest level of bactericidal activity.

FIG. 5A), a control non-trangenic plant (FIG. 5B), and a ECEMA-expressing plant (2X35S ECEMA; FIG. 5C) after infection with *Phytophthora infestans* (US-8 isolate).

FIGS. 6A–6D are digital images of respective transgenic potato plants challenged with a fungal pathogen *Phytophthora cactorum*. After rooting in MS medium, the control (FIG. 6A) and ECEMA transgenic (FIG. 6B) Russet Burbank plants, and the control (FIG. 6C) and ECEMA transgenic (FIG. 6D) Desiree plants were challenged with the fungus *Phytophthora cactorum*. Pictures were taken 11 days (FIGS. 6A and 6B) or 19 days (FIGS. 6C and 6D) after infection. The control plants were heavily infected while the transgenic plants were still green and growing.

DETAILED DESCRIPTION OF THE INVENTION

I. Definitions

Figures 1A, 1B:
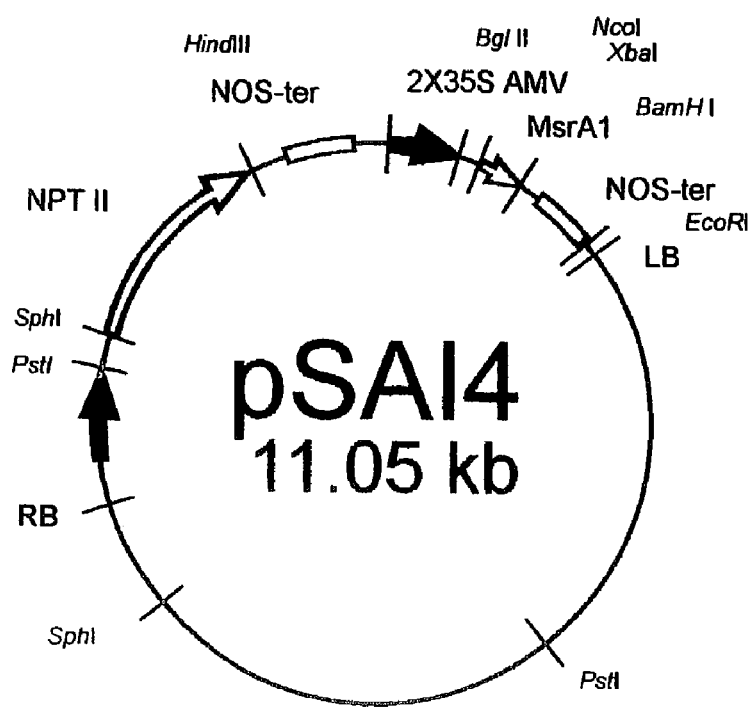
FIGS. 1A and 1B show the structure and expression constructs for ECEMA.

Unless otherwise noted, technical terms are used according to conventional usage. Definitions of common terms in molecular biology may be found in Lewin, *Genes VII*, Oxford University Press, 1999 (ISBN 0-19-879276-X); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: a Comprehensive Desk Reference*, VCH Publishers, Inc., 1995 (ISBN 1-56081-569-8).

"CEMA and CEMA-related peptides." The phrase "CEMA and CEMA-related peptides" refers to the CEMA peptide, which contains 8 amino acid residues from the N-terminus of cecropin A and a modified mellitin sequence at the C-terminus (Hancock et al., U.S. Pat. No. 5,707,855), as well as variants of the CEMA peptide described supra. The variants of the CEMA peptide can contain additional amino acid sequences operably linked to the CEMA amino acid sequence (SEQ ID NO: 1) or fragments of the CEMA amino acid sequence. The additional amino acid sequences can be either pro-regions, spacer sequences, N-terminal extensions, or C-terminal extensions, as described below. The variants of CEMA also can contain one or more conservative amino acid substitutions as described below. However, the CEMA and CEMA-related peptides encompassed by the invention are characterized, at least in part, by their respective abilities to confer disease resistance upon expression of the respective peptides in a plant, while not substantially affecting the growth and health of the plant. As described herein, some transgenic plants may display various morphological differences when compared to their non-transgenic counterparts. However, these plants will maintain resistance to a broad spectrum of pathogens and be capable of growth.

An example of a CEMA-related peptide is the peptide termed "ECEMA" (SEQ ID NO: 4). ECEMA consists of 34 amino acids including 8 amino acids from cecropin A and 16 amino acids from mellitin with extensions on both the N-(6 residues) and C-(4 residues) termini. The 6-amino-acid N-terminal extension contains the sequence MALEHM (SEQ ID NO: 11).

In addition to using CEMA and CEMA-related peptides as described above, it will be apparent to one of ordinary skill in the art that the invention may be practiced using peptides that vary somewhat from the naturally occurring antibacterial peptides, while nevertheless conferring enhanced broad-spectrum pathogen resistance when expressed in plants.

"CEMA and CEMA-related peptide biological activity." The phrase "CEMA and CEMA-related peptide biological activity" refers to the ability of a CEMA or CEMA-related peptide, such as ECEMA, to inhibit bacterial growth and/or fungal growth. CEMA and CEMA-related peptide biological activity can be readily ascertained using the protocols given below.

The antibacterial activity of a given CEMA and/or CEMA-related peptide can be assessed conveniently by determining the ability of the peptide to inhibit the growth of a pectinolytic bacterial strain such as *Erwinia carotovora* or even *Escherichia coli* DH5α. The activity of a given peptide is determined by serially diluting the peptide in Luria-Bertaini (LB) medium and 100-µL aliquots of the resulting titers into wells of a 96-well microtiter plate. A fresh bacterial culture (~0.3 $A_{550}$) is then grown on LB medium (1% w/v tryptone and 0.5% w/v yeast extract) and diluted to $10^{-2}$ in LB to represent approximately $10^{4-105}$ colony forming units (CFU)mL$^{-1}$. 10 µL of the bacterial culture are then inoculated into each well containing the peptide and the samples are incubated at 37° C. for 4 hours. The well contents are then diluted in LB, plated on LB agar, and incubated overnight at an appropriate temperature. The number of bacterial colonies that grow on each plate corresponds to the respective dilution of CEMA and/or CEMA-related peptide (the control plate contains no added peptide). The colonies are counted, and the antibacterial activity of the peptide under test is determined by comparison to the control plate.

The CEMA or CEMA-related peptide is determined to have biological activity if, under the conditions of this assay, the peptide is capable of inhibiting bacterial growth by at least 10% (compared to the control) at a concentration of 7 µg per mL (i.e., at this concentration, the number of bacterial colonies is no more than 90% that of the control plate).

The antifungal activity of a given CEMA or CEMA-related peptide is assessed by utilizing the fungal strains *Phytophthora cactorum, Phytophthora infestans*, and/or *Fusarium solani*. The selected fungal strain is grown on Five Cereal Agar (FCA, containing 20 gL$^{-1}$ "instant" flakes of five-cereal baby food, and 8 gL$^{-1}$ agar (Terras et al., *Plant Cell* 7:573–588, 1995). After 5 days' growth at room temperature, a mycelial plug is removed and placed upside down in the center of a fresh FCA plate. A sterile solution (10:1) of the test peptide is then introduced into a well 3 cm from the edge of the plate, and a control well containing sterile water is established on the same plate. Various concentrations of the test peptide may be tested on the same plate, or on other plates. The assay plates are incubated for 5 days at room temperature, after which the zone of growth inhibition around each well is measured.

The CEMA or CEMA-related peptide is determined to have biological activity if, under the conditions of this assay, it is capable of inhibiting fungal growth at a concentration of up to 10 µg per mL compared to the control (i.e., there is a discernible zone of inhibition of fungal growth around a well containing this concentration of peptide).

"Terminal Extensions." As used herein the term "terminal extensions" refers to added sequences, such as those shown in SEQ ID NOS: 5–7 and 11, at either the N-terminus or the C-terminus of a peptide. For example, an N-terminal extension is illustrated by the sequence MALEHM (SEQ ID NO: 11) that is added onto the N-terminus of a cationic peptide such as CEMA (SEQ ID NO: 2). In the discussion below, when reference is made to N-terminal extensions it should be understood to refer to either N- or C-terminal extensions.

N-terminal extensions are characterized by their ability to modulate the anti-microbial activity of the cationic peptide, i.e., either increasing or decreasing anti-microbial activity. The present disclosure provides assays that can be used to test the anti-microbial activity of an extended cationic peptide. An N-terminal extension is found to modulate the anti-microbial activity of a cationic peptide if it either increases or decreases the peptide's anti-microbial activity when compared its non-extended counterpart. However, some N-terminal extensions will be found to substantially alter the anti-microbial activity such as by altering the anti-microbial activity of a given peptide by at least 10%, 20%, 30%, 40%, 50%, or 60% when compared to the peptide's non-extended counterpart.

For example, using the anti-bacterial assay described below, CEMA (SEQ ID NO: 2) kills 50% of bacterial cells (*E. coli*) at 4.5 µg/mL, and ECEMA (SEQ ID NO: 4) kills 50% of bacterial cells (*E. coli*) at 36 µg/mL. Hence, ECEMA (SEQ ID NO: 4) is 8–10 times less toxic than CEMA (SEQ ID NO: 2). Similarly, when tested against *E. carotovora*, ECEMA is 15–20 times less toxic than CEMA (SEQ ID NO: 2).

In addition to being characterized by their activity, N-terminal extensions are also characterized by their length. Typically, N-terminal extensions are no more than 25 amino acid residues long, and in many cases N-terminal extensions are no more than 20, 15, 10, or 5 amino acids long. The length of a particular extension will depend in part on the level of anti-microbial activity that is desired, and the anti-fungal and anti-bacterial assays described herein can be used to assay the N-terminally extended cationic peptides.

"Transgenic plant." As used herein a "transgenic plant" refers to a plant that contains recombinant genetic material ("transgene") not normally found in a wild-type plant of the same species. Thus, a plant that is grown from a plant cell into which recombinant DNA is introduced by transformation is a transgenic plant, as are all offspring (whether produced sexually or asexually) of that plant that contain the introduced transgene. "Transgenic plant" also refers to a plant when the transgene resides in a plastid, such as a chloroplast, amyloplasts, etioplasts, chromoplasts, etc. Such plastids are abundant and inherited maternally.

"Cationic peptide." The term "cationic peptide" refers to a sequence of amino acids from about 5 to about 50 amino acids in length and preferably from about 15 to about 35 amino acids in length. A peptide is "cationic" if it possesses sufficient positively charged amino acids that has a $pK_a$ greater than 9.0. Typically, at least four of the amino acid residues of the cationic peptide can be positively charged, for example, lysine or arginine. "Positively charged" refers to the side chains of the amino acid residues which have a net positive charge at pH 7.0. Examples of naturally occurring cationic peptides which can be recombinantly produced according to the invention include defensins, magainins, melittin, and cecropins, dermaseptins, temporins, and analogs thereof.

"Sequence Identity." The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison purposes are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237–244, 1988; Higgins and Sharp, *CABIOS* 5:151–153, 1989; Corpet et al., *Nucleic Acids Research* 16:10881–10890, 1988; Huang, et al., *Computer Applications in the Biosciences* 8:155–165, 1992; and Pearson et al., *Methods in Molecular Biology* 24:307–331, 1994. Altschul et al., *J. Mol. Biol.,* 215:403–410, 1990, presents a detailed consideration of sequence-alignment methods and homology calculations.

The NCBI Basic Local Alignment Search Tool (BLAST™, Altschul et al., *J. Mol. Biol.,* 215:403–410, 1990) is available from several sources, including the National Center for Biotechnology Information (NCBI, Bethesda, Md.) and on the Internet, for use in connection with the sequence-analysis programs BLASTP, BLASTN, BLASTX, TBLASTN, and TBLASTX. BLAST™ can be accessed on the Internet.

For comparisons of amino acid sequences of greater than about 30 amino acids, the "Blast 2 sequences" function in the BLAST™ program is employed using the default BLOSUM62 matrix set to default parameters, (gap existence cost of 11 and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins having even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

"Recombinant." A "recombinant" nucleic acid is one having a sequence that is not naturally occurring or has a sequence made by an artificial combination of two otherwise separated, shorter sequences. This artificial combination is often accomplished by chemical synthesis or, more commonly, by the artificial manipulation of isolated segments of nucleic acids, e.g., by genetic engineering techniques.

"Oligonucleotide ("oligo")." An "oligonucleotide" refers to a linear polynucleotide sequence of up to about 100 nucleotide bases in length.

"Probes and primers." Nucleic acid probes and primers may be prepared readily based on the nucleic acid sequences provided by this invention. A "probe" comprises an isolated nucleic acid sequence attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (eds.), *Molecular Cloning: A Laboratory Manual,* 2nd ed., vol. 1–3, Cold Spring Harbor Laboratory Press, Cold Spring Harbor, N.Y., 1989; and Ausubel et al. (eds.), *Current Protocols in Molecular Biology,* Greene Publishing and Wiley-Interscience, New York (with periodic updates), 1987.

"Primers" are short nucleic acids, preferably DNA oligonucleotides 15 nucleotides or more in length, that are annealed to a complementary target DNA strand by nucleic acid hybridization to form a hybrid between the primer and the target DNA strand, then extended along the target DNA strand by a DNA polymerase. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length, but, to enhance specificity, probes and primers of 20 or more nucleotides may be preferred.

Methods for preparing and using probes and primers are described, for example, in Sambrook et al. (ed.), *Molecular Cloning: A Laboratory Manual,* 2nd ed., vol. 1–3, Cold Spring Harbor Laboratory Press, Cold Spring Harbor, N.Y., 1989; Ausubel et al. (eds.), *Current Protocols in Molecular Biology,* Greene Publishing and Wiley-Interscience, New York (with periodic updates), 1987; and Innis et al., *PCR Protocols: A Guide to Methods and Applications,* Academic Press: San Diego, 1990. PCR primer pairs can be derived from a known sequence, for example, by using computer programs intended for that purpose such as Primer™ (Version 0.5, 1991, Whitehead Institute for Biomedical Research, Cambridge, Mass.). One of skill in the art will appreciate that the specificity of a particular probe or primer increases with the length of the probe or primer. For example, a primer comprising 20 consecutive nucleotides will anneal to a target with a higher specificity than a corresponding primer of only 15 nucleotides. Thus, in order to obtain greater specificity, probes and primers may be selected that comprise, by way of example, 10, 20, 25, 30, 35, 40, 50 or more consecutive nucleotides.

"Isolated." An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

"Vector." A "vector" is a nucleic acid molecule as introduced into a host cell, thereby producing a transformed host cell. A vector may include one or more nucleic acid sequences, such as an origin of replication, that permit the vector to replicate in a host cell. A vector may also include one or more selectable marker genes and other genetic elements known in the art.

"Operably linked." A first nucleic acid sequence is "operably linked" with a second nucleic acid sequence whenever the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. Two peptide sequences may be operably linked through a normal peptide bond, or by other covalent linkage.

"Transformed." A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, transformation with a chloroplast vector into chloroplasts, and introduction of naked DNA by electroporation, lipofection, microinjection and particle gun acceleration.

II. Selection of CEMA Peptides a. CEMA and/or CEMA-Related Peptides

A listing of the exemplary CEMA and CEMA-related peptides (ECEMA) is provided above. Nucleic acid molecules encoding the CEMA and ECEMA peptides may be derived by simple application of the genetic code to the peptide sequence. For example, the amino acid sequence of the CEMA peptide is provided in SEQ ID NO: 1 and the amino acid sequence encoding ECEMA is shown in SEQ ID NO: 4.

One of ordinary skill in the art will appreciate that the various CEMA and ECEMA peptides exhibit different degrees of anti-microbial activity, with some working more effectively against certain pathogens than others. Hence, when selecting peptides for producing transgenic plants with enhanced pathogen resistance, the selection of a particular CEMA-related peptide will be depend upon, among other factors, the type of plant in which the peptide is to be expressed, and the types of pathogens that commonly infect that plant type.

Having selected the desired CEMA peptide or CEMA-related peptide to be expressed, a nucleic acid molecule encoding the peptide may be produced by standard molecular biology techniques. Because the CEMA and CEMA-related peptides are relatively short, a simple way to synthesize the nucleic acid molecule is by synthesis of overlapping oligonucleotides on a commercially available oligonucleotide synthesizer. The oligonucleotides are then assembled into a fill-length coding region in vitro. This approach also permits the selection of codons encoding particular amino acid residues that reflect the codon-usage bias of the plant into which the nucleic acid molecule is to be introduced, thereby enhancing the expression efficiency. Detailed examples of the production of coding sequences using this approach are provided in the Examples below.

b. Addition of Other Peptide Sequences

The CEMA and CEMA-related peptides may be also expressed in transgenic plants in the form of fusion proteins. Although any desired peptide may be fused to the selected CEMA and/or CEMA-related peptide for expression in plants, the expression of fusion proteins comprising an anionic pro-region peptide operably linked to the amino terminus of the CEMA, or CEMA-related peptide would be particularly beneficial. Any anionic pro-region peptide may be employed for this purpose, including the anionic pro-regions that are found in naturally occurring full-length (i.e., unprocessed) antimicrobial peptides. For example, the pro-region comprising amino acids 23–46 of temporin G (shown in SEQ ID NO: 8) may be used as a pro-region. Such pro-region peptides serve to neutralize the cationic nature of the antimicrobial peptide and thus, may provide enhanced stability in the cellular environment. To such end, these pro-regions generally include a number of negatively charged amino acids, such as glutamate (Glu or E) and aspartate (Asp or D).

Examples of other naturally occurring pro-region peptides that are known in the art include pro-region peptides of the following proteins: the human neutrophil defensin protein (Daher et al., *Proc. Natl. Acad. Sci. USA*, 85:7327–7331, 1988); the bovine antimicrobial cathelicidin protein BMAP28 (Skerlavaj et al., *J. Biol. Chem.* 271:28375–28381, 1996); the sheep antimicrobial cathelin family of proteins (Mahoney et al., *FEBS Lett.* 377:519–522, 1995); bovine indolicidin (Del Sal et al., *Biochem. Biophys. Res. Commun.* 187:467–472, 1992); the porcine antimicrobial peptides prophenin-2 and PR-39 (Zhao et al., *FEBS Lett.* 367:130–134, 1995) and PMAP-37 (Tossi et al., *Eur. J. Biochem.* 15:941–946, 1995); the human antimicrobial lipopolysaccharide binding protein CAP18 (Larrick, et al., *FEBS Lett.* 398(1):74–80, 1996); and the murine protein E3 (Scott and Collins, *Blood* 88:2517–2530, 1996).

Whereas the anionic pro-region peptide may be directly joined to the N-terminus of the cationic peptide, an alternative embodiment involves linking the pro-region peptide to CEMA and/or a CEMA-related peptide using a spacer peptide sequence. The use of spacer peptides to join two peptide domains is well known in the art; such spacer peptides are typically of between 2 and 25 amino acids in length, and provide a flexible hinge connecting the first peptide sequence to the second peptide. Spacer sequences that have been used to provide flexible hinges connecting two peptide sequences include the glycine(4)-serine spacer (GGGGS x3: SEQ ID NO: 12) described by Chaudhary et al., Nature 339:394–397, 1989. Alternatively, an N-terminal peptide extension as described below can provide the spacer peptide function. Spacer sequence peptides may also include a cleavage site, such as a peptide sequence recognized and cleaved by a protease, such as Factor Xa. Such sites facilitate removal of the pro-region from the CEMA and/or CEMA-related peptide following purification from plant tissues. The use of anionic pro-region peptides and spacer peptides to express certain cationic peptides in microbial systems is known in the art and described in U.S. Pat. No. 5,707,855 to Hancock.

In certain embodiments, an N-terminal extension peptide sequence may be added to the CEMA and/or CEMA-related peptide. These N-terminal peptide extensions may serve to provide enhanced resistance to proteolytic cleavage, enhanced transcription levels, and/or increase or decrease the anti-microbial activity of the peptides such that the expressed peptides are compatible with the specific physiology of the plant species while providing adequate anti-microbial activity. Typically, these N-terminal extensions are of between 2 and 25 amino acids in length, although longer extensions also may be employed. Examples of N-terminal extension sequences that are utilized in certain embodiments include the peptide sequences shown in SEQ ID NOS: 5–7, and 11. In each case, an N-terminal methionine is added to ensure proper expression of the peptide. One of ordinary skill in the art will appreciate that the effect of adding any particular N-terminal extension may be assessed readily using the biological activity assays described herein.

d. Variant CEMA and CEMA-Related Peptides

The nucleic acid sequence encoding CEMA or a CEMA-related peptide can be manipulated so that it encodes a variant CEMA or CEMA-related peptide. This can be done through a variety of methods, for example by using site-directed mutagenesis or the polymerase chain reaction (PCR). Alternatively, because the peptides are relatively short molecules, the coding region for a variant peptide can be synthesized simply de novo and introduced into a suitable expression vector.

The simplest modifications of amino acid sequences involve the substitution of one or more amino acids for amino acids having similar biochemical properties. These so-called "conservative substitutions" are likely to have minimal impact on the activity of the resultant peptide. Thus, peptides that differ by one or more conservative amino acid substitutions may be used in the invention in place of CEMA (SEQ ID NO: 2) and CEMA-related peptides, such as ECEMA (SEQ ID NO: 4). Table 1 shows amino acids that may be substituted for a respective original amino acid in a protein and that are regarded as conservative substitutions.

TABLE 1

| Original Residue | Conservative Substitutions |
|---|---|
| ala | ser |
| arg | lys |
| asn | gln; his |
| asp | glu |
| gln | asn |
| glu | asp |
| gly | pro |
| his | asn; gln |
| ile | leu; val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

More substantial changes in function or any of various other features of a subject peptide may be obtained by selecting substitutions that are less conservative than those in Table 1, i.e., by selecting residues that differ more significantly in their effect on maintaining: (a) the structure of the polypeptide backbone in the area of the substitution, for example, as a sheet or helical conformation, (b) the charge or hydrophobicity of the molecule at the target site, or (c) the bulk of the side chain. The substitutions that, in general, are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. Variant peptides having one or more of these more substantial changes also may be employed in the invention, provided that CEMA biological activity is retained.

More extensive amino acid changes also may be engineered into variant CEMA or ECEMA peptides. As noted above, however, such a variant peptide typically will be characterized as possessing at least 40% sequence identity determined over a full-length alignment with the amino acid sequence of the respective naturally occurring amino acid sequence using any of the alignment programs described above. In addition, these variant peptides will retain biological activity.

Confirmation that a variant CEMA peptide has biological activity may be achieved using any of the assay systems described above. Following confirmation that the peptide has the desired activity, a nucleic acid molecule encoding the peptide can be produced readily using standard molecular biology techniques. Where appropriate, the selection of the open reading frame will take into account codon-usage bias of the plant species in which the peptide is to be expressed.

III. Introducing CEMA and CEMA-Related Peptides into Plants

After a nucleic acid sequence encoding a CEMA or a CEMA-related peptide, such as ECEMA, has been produced, standard techniques may be used to express the sequence in a transgenic plant in order to confer pathogen resistance to the plant. The basic approach is to clone the nucleic acid into a transformation vector, such that the nucleic acid is operably linked to a control sequence (e.g., a promoter) that directs expression of the nucleic acid in a plant cell. The transformation vector is then introduced into plant cells by any of a number of techniques (e.g., electroporation). Whole plants are generated from the cells, and progeny plants containing the introduced nucleic acid are selected. Desirably, all or part of the transformation vector stably integrates either into the genome of the plant cell or into the genome of an organelle such as mitochondria and/or chloroplasts. That part of the transformation vector that integrates into the plant cell and that contains the introduced sequence and associated sequences for controlling expression (the introduced "transgene") may be referred to as the recombinant expression cassette.

Selection of progeny plants containing the introduced transgene may be performed based upon the detection of an altered phenotype. Such a phenotype may result directly from disease resistance conferred by the introduced sequence or may be manifest as an exhibited enhanced resistance to a chemical agent (such as an antibiotic) due to the dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods")

U.S. Pat. No. 5,677,175 ("Plant Pathogen Induced Proteins")

U.S. Pat. No. 5,510,471 ("Chimeric Gene for the Transformation of Plants")

U.S. Pat. No. 5,750,386 ("Pathogen-Resistant Transgenic Plants")

U.S. Pat. No. 5,597,945 ("Plants Genetically Enhanced for Disease Resistance")

U.S. Pat. No. 5,589,615 ("Process for the Production of Transgenic Plants with Increased Nutritional Value Via the Expression of Modified 2S Storage Albumins")

U.S. Pat. No. 5,750,871 ("Transformation and Foreign Gene Expression in Brassica Species")

U.S. Pat. No. 5,268,526 ("Overexpression of Phytochrome in Transgenic Plants")

U.S. Pat. No. 5,780,708 ("Fertile Transgenic Corn Plants")

U.S. Pat. No. 5,538,880 ("Method For Preparing Fertile Transgenic Corn Plants")

U.S. Pat. No. 5,773,269 ("Fertile Transgenic Oat Plants")

U.S. Pat. No. 5,736,369 ("Method For Producing Transgenic Cereal Plants")

U.S. Pat. No. 5,610,042 ("Methods For Stable Transformation of Wheat").

U.S. Pat. No. 5,576,198 (Controlled expression of transgenic constructs in plant plastids)

These examples include descriptions of transformation-vector selection, transformation techniques, and the construction of constructs designed to over-express the introduced transgene.

a. Plant Types

Diseases caused by any of various pathogens affect a wide variety of plant species. Susceptible plants include monocots, dicots, and gymnosperms. Thus, for example, CEMA and/or CEMA-related peptides may be introduced into plant species including, but not limited to, maize, wheat, rice, barley, soybean, cotton, legumes, rape/canola, alfalfa, flax, sunflower, safflower, brassica, cotton, tobacco, flax, peanut, clover, cowpea, and grapes; vegetables such as lettuce, tomato, cucurbits, cassava, potato, carrot, radish, pea, lentils, cabbage, cauliflower, broccoli, Brussels sprouts, and peppers; tree fruits such as citrus, apples, pears, peaches, apricots, and walnuts; trees such as Douglas fir, loblolly pine, poplar, and elms; flowers such as carnations, roses, lilies; and cacao, coffee, and rubber.

b. Vector Construction and Choice of Promoters

A number of recombinant vectors suitable for stable transfection of plant cells or for the establishment of transgenic plants have been described, including those described in Pouwels et al., *Cloning Vectors: A Laboratory Manual,* 1987; Weissbach and Weissbach, *Methods for Plant Molecular Biology*, Academic Press, 5:173–184, 1989; and Gelvin et al., *Plant Molecular Biology Manual*, Kluwer Academic Publishers, 1990. Typically, a plant-transformation vector includes one or more cloned sequences under the transcriptional control of 5'- and 3'-regulatory sequences and a dominant selectable marker. Such a plant-transformation vector typically also contains a promoter regulatory region (e.g., a regulatory region controlling inducible or constitutive expression, environmentally regulated or developmentally regulated expression, or cell-specific or tissue-specific expression), a transcription-initiation site, a ribosome-binding site, an RNA-processing signal, a transcription-termination site, and/or a polyadenylation signal.

Examples of constitutive plant promoters that may be useful for expressing a transgene include: the cauliflower mosaic virus (CaMV) 35S promoter, which confers constitutive, high-level expression in most plant tissues (see e.g., Odel et al., *Nature* 313:810, 1985; Dekeyser et al., *Plant Cell,* 2:591, 1990; Terada and Shimamoto, *Mol. Gen. Genet.* 220:389, 1990; and Benfey and Chua, *Science* 250:959–966, 1990); the nopaline synthase promoter (An et al., *Plant Physiol.* 88:547, 1998); the octopine synthase promoter (Fromm et al., *Plant Cell* 1:977, 1989); the 2x CaMV/35S promoter with a translational enhancer sequence (Kay et al., *Science* 236:1299–1302, 1987); and chloroplast 16S rRNA promoter (Daniell et al., *Nat. Biotech.* 16:345–348, 1998).

Any of a variety of plant-gene promoters that are regulated in response to environmental, hormonal, chemical, and/or developmental signals, also can be used for expression of a transgene in plant cells, including promoters regulated by one or more of: (a) heat (Callis et al., *Plant Physiol.* 88:965, 1988; Ainley et al., *Plant Mol. Biol.,* 22:13–23, 1993; and Gilmartin et al., *Plant Cell* 4:839–949, 1992); (b) light (e.g., the pea rbcS-3A promoter, Kuhlemeier et al., *Plant Cell* 1:471, 1989 and the maize rbcS promoter, Schaffner and Sheen, *Plant Cell* 3:997, 1991); (c) hormones, (e.g., abscisic acid, Marcotte et al., *Plant Cell* 1:471, 1989); (d) wounding (e.g., the potato PinII promoter, Keil et al., *Nucl. Acids. Res.* 14:5641–5650, 1986, the *Agrobacterium* mas promoter, Langridge et al., *Bio/Technology* 10:305–308, 1989, and the grapevine vst1 promoter, Weise et al., *Plant Mol. Biol.* 26:667–677, 1994); and (e) chemicals (e.g., methyl jasmonate or salicylic acid, Gatz et al., *Plant Mol. Biol.* 48:89–108, 1997).

Alternatively, a tissue-specific (root, leaf, flower, and seed, for example) promoter (Carpenter et al., *Plant Cell* 4:557–571, 1992; Denis et al., *Plant Physiol.* 101:1295–1304, 1993; Opperman et al., *Science* 263:221–223, 1993; Stockhause et al., *Plant Cell* 9:479–489, 1997; Roshal et al., *EMBO J.* 6:1155, 1987; Schernthaner et al., *EMBO J.* 7:1249, 1988; Yamamoto et al., *Plant Cell* 3:371–382, 1990; and Bustos et al., *Plant Cell* 1:839, 1989) can be fused to the coding sequence to obtain a particular expression in a respective organ.

A plant-transformation vector also may include an RNA-processing signal, for example, an intron, which may be positioned upstream or downstream of the ORF sequence in the transgene. In addition, the expression vector may also include additional regulatory sequence from the 3'-untranslated region of a plant gene, e.g., a 3' terminator region to increase mRNA stability of the mRNA, such as the PI-II terminator region of potato or the octopine or nopaline synthase (NOS) 3' terminator regions.

Finally, as noted above, a plant-transformation vector may also include a dominant selectable marker gene to allow for the ready selection of transformants. Such genes include those encoding antibiotic resistance (e.g., resistance to hygromycin, kanamycin, bleomycin, G418, streptomycin, or spectinomycin) and herbicide resistance (e.g., phosphinothricin acetyltransferase).

c. Transformation and Regeneration Techniques

Transformation and regeneration of both monocotyledonous and dicotyledonous plant cells and organelles are now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG)

mediated transformation; transformation using viruses; micro-injection of plant cells; micro-projectile bombardment of plant cells; vacuum infiltration; *Agrobacterium tumefaciens* (AT)-mediated transformation; and chloroplast transformation. Typical procedures for transforming and regenerating plants are described in the patent documents listed at the beginning of this section.

d. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

Selection also can be accomplished by exploiting the pathogen resistance that is conferred to the plant via the transgene. As described in the Examples below, such screening may be accomplished either after the transgenic plants have been regenerated, or (depending on the transformation method used) may be performed on green transgenic callus prior to plant regeneration.

IV. Plants Containing Coding Regions for Multiple Cationic Peptides

In some cases, the level of resistance that is conferred by a single copy of a transgene encoding a CEMA or CEMA-related peptide may be enhanced by introducing multiple copies of a single cationic peptide gene, or several genes encoding different cationic peptides.

Through the use of genetic engineering, it is possible to introduce coding regions for multiple cationic peptides into a single vector. Typically (although not necessarily) such vectors comprise two or more CEMA and/or CEMA-related open reading frames (ORFs) each operably linked to its own 5'- and 3'-regulatory sequences. When introduced into plants, such vectors can result in the expression of multiple varieties of cationic peptides.

The creation of a plant containing multiple transgenes also can be accomplished through the use of standard breeding techniques. A transgene encoding a first cationic peptide can be introduced into a first plant and a second transgene encoding a second cationic peptide can be introduced into a second plant. The resulting transgenic plants then can be crossed to produce progeny that carry both transgenes.

V. Production and Isolation of CEMA and CEMA-Related Peptides

The compositions and methods described above may be used not only for producing plants exhibiting an enhanced, broad-spectrum pathogen resistance, but also for the large-scale production of CEMA and CEMA-related peptides for a wide range of other applications. For example, CEMA and CEMA-related peptides produced in large quantities in plants may be purified and used in medical applications. Another aspect of the invention provided plants producing CEMA and CEMA related peptides that may be used as medicinal plants without further purification of the cationic peptide. Such plants may be used to treat or prevent diseases such as infectious microbial diseases, and/or cancer in animals, such as humans.

The production of biologically active peptides in plants is now widely practiced, and bulk expression and purification methods are well known. Examples of constructs that facilitate the production of biologically active proteins in plants can be found in U.S. Pat. No. 4,956,282 to Goodman et al. These constructs generally contain a promoter region and an additional nucleic acid sequence that encodes an amino acid sequence that is later utilized in the purification process. The amino acid sequence that is used to facilitate the isolation of the CEMA and/or CEMA-related peptides can be subsequently cleaved and discarded.

Production of biologically active peptides in plants may be enhanced by transformation and expression in intracellular organelles such as in a chloroplast. In these instances the organelle could serve to enhance expression as well as contain the peptide thus preventing plant toxicity through overexpression. These organelles then would be a source of highly concentrated CEMA or CEMA related peptides from which the peptides could be isolated.

VI. Production of CAPs with N-Terminal Extensions

The ECEMA molecule described herein is an example of an N-terminally extended CAP. One of skill in the art will appreciate that other CAPs can be modified to contain N-terminal extensions and that by adding additional amino acids residues onto CAPs, the activity of the CAP will be modified and in some cases allow the CAP to be used successfully to protect plants from a broad spectrum of pathogens (wherein "broad-spectrum resistance means resistance at least one fungal strain and resistance to at least one bacterial strain).

Accordingly, the invention provides methods of adding N-terminal extensions to CAPs and testing the extended CAP's resulting activity in vitro. The invention also provides methods of testing such N-terminally extended CAPs in plants. Examples of N-terminal extensions are provided in SEQ ID NOS: 5–7, and 11. Additionally, variants of such extensions can be made without altering the N-terminal extensions ability to render the expression of the CAP compatable with plant physiology, i.e., allowing the plant to grow. The variants can include conservative amino acid substitutions, deletions, and additions, as described above. These variant N-terminal extensions, however, will maintain sufficient antimicrobial activity such that, upon expression in plants, they can enhance the plant's resistance to a broad spectrum of pathogens.

VI. Conferred Resistance

The mechanism of cell-to-cell trafficking of proteins is not well understood. However, it is known that various movement proteins isolated from viruses facilitate the movement of proteins from cell to cell (Lucas and Wolf, *Current Opinion in Plant Biology* 2:192–197, 1999; and Lazarowitz, *Current Opinion in Plant Biology* 2:332–338, 1999). Additionally, phloem fluid has been found to contain numerous proteins and the presence of such proteins has been correlated with long-distance delivery of macromolecules such as proteins (Thompson, *Trends in Plant Science* 4:354–360, 1999). Hence it is likely that, when transgenic plant tissue expressing CEMA or a CEMA-related peptide is grafted onto other non-transgenic tissue, the transgenic tissue will confer at least some pathogen resistance to the non-transgenic portion. Pathogen resistance that is imparted to a non-transgenic plant tissue is herein referred to as "conferred resistance." This "conferred resistance" can be established either by grafting a scion (upper vegetative tissue) onto a transgenic stock (lower vegetative tissue), or by grafting a transgenic scion onto a non-transgenic stock. Plants produced by such grafting are herein after referred to as "chimeric plants."

It additionally is anticipated that infiltration of the non-transgenic tissue can be increased by co-expressing or operably linking the CEMA or CEMA-related protein with viral-movement proteins or other proteins that are normally found in the phloem.

A grafting protocol can be made more flexible by utilizing cross-species grafting. Thus, a graft from, e.g., almond (*Prunus amygdalus*) can be placed on stock from peach (*Prunus persica*). Such flexibility increases the range of plants for which a given transgenic tissue can be used. For example, after almond tissue containing the CEMA or CEMA-related peptide has been generated, the resulting transgenic tissue can be used to confer resistance not only to other almond trees, but also to peach trees.

The use of conferred resistance also decreases the possibility that a transgene made according to the invention will be introduced into the environment. This is because the resistance is derived from the graft itself and the rest of the plant remains free of the transgene. Therefore, the fruits and seeds of the plant can be left non-transgenic, so as not to transmit the gene.

By preventing a transgene from being systemically introduced into the plant, products for human consumption can be produced by the plant that are not transgenic.

Furthermore, chimeric plants such as those described above do not necessarily have to confer pathogen resistance to the non-transgenic tissue. In some instances the transgenic portion of the chimeric plant may be desirable to provide pathogen resistance to just the transgenic tissue.

EXAMPLES

1. Selection and Creation of Nucleic Acid Sequences Encoding the CEMA and CEMA-Related Peptides The primers (Oligo #1: 5'-CAAGG AAAAA CGGTC TAGAG CATAT GAAAT GGAAA C-3' (SEQ ID NO: 9); and Oligo #2: 5'-GAACT CGAGC AGCGA GCTCT TACTT AGTTA GCTTC-3' (SEQ ID NO: 10)) were configured to have an XbaI recognition site at the 5'-end, and an BamHI-recognition site at the 3'-end of the amplified fragment, respectively. Plasmid pR78hproCEMA (R. E. W. Hancock, Vancouver, B.C.; Piers, et al., *Antimicrob. Agents Chemother.* 38:2311–2316, 1994) was used as a template for PCR. An amplified DNA fragment containing the sequence encoding ECEMA was purified using a NucleoSpin™ column (CLONTECH, Palo Alto, Calif., USA), digested with XbaI and BamHI, and inserted into the vector (Promega Corp., Madison, Wis., USA) that had previously been digested with XbaI and BamHI. The resulting vector was named pSAII.

The HindIII-EcoRI fragment in pBI121 (Clontech), containing a CaMV 35S promoter, a GUS gene, and NOS-ter sequences, was excised and replaced by the HindIII-EcoRI fragment from pSAI1 (containing an enhanced 35S promoter with an AMV RNA4 translation-enhancing element, the ECEMA coding sequence (SEQ ID NO: 3), and NOS-ter sequences). The resulting vector was specified as pSAI4. The double-stranded DNA encoding ECEMA then was cloned into one or more of the vectors described below.

2. Vectors Containing Various Promoter Sequences

The nucleic acid sequences encoding ECEMA and CEMA were assembled into various plant-transformation vectors, thereby placing the sequences under the transcriptional control of a variety of different respective promoters.

Cloning nucleic acid sequences encoding ECEMA and CEMA into one such vector placed the respective sequence under the control of a promoter that contained two copies of the CaMV 35S promoter and an AMV RNA4 translation-enhancing element. Kay et al., *Science* 236:1299–1302, 1987. The clones that were produced from such a vector were designated with the prefix "pD." Hence, for example, pDECEMA designates a vector that contains the ECEMA construct under the control of the double CaMV 35S promoter and the AMV RNA4 translational enhancer, and pDCEMA designates a vector that contains the CEMA construct under the control of the double CaMV 35S promoter and the AMV RNA4 translational enhancer.

Another vector was configured such that the ECEMA-coding sequence was under the control of a rebuilt "super promoter." The clones that were produced from such a vector were designated pRSHECEMA. The super promoter contained the mas (mannopine synthase) promoter/activator region (Langridge et al., *Bio/Technology* 10:305–308, 1989) preceded by a trimer of ocs (octopine synthase) upstream activating sequence (in inverted orientation). A more detailed description of this super promoter is provided in Ni et al., *The Plant J.* 7:661–676, 1995.

A nucleic acid sequence encoding CEMA was cloned into another vector that contained a single copy of the CaMV 35S promoter and the pro-region from human neutrophil defensin protein (Daher et al., *Proc. Natl. Acad. Sci USA,* 85:7327–7331, 1988). The resulting vector was designated "pProCEMA".

3. Transformation of Potato and Tobacco

The Potato cultivars, "Russet Burbank" and "Desiree," as well as tobacco, were used as representative plant species for transformation. Plant transformation was performed according to De Block, *Theoret. Appl. Genet.* 76:767–774, 1988, with some modifications. Transformation of *Agrobacterium tumefaciens* LBA4404 or MP90 was performed by the freeze-thaw method described in Holster, et al., *Mol. Gen. Genet.* 163:181–187, 1978.

Transformed *Agrobacterium* cells were plated on selective media (LB+100 μg/mL rifampicin+50 μg/mL kanamycin for LBA4404; LB+10 μg/mL gentamycin+50 μg/mL kanamycin for MP90). The presence of the plasmid pSAI4 in *Agrobacterium* cells was confirmed by plasmid isolation and restriction analysis.

Transformation of the potato cultivars "Desiree" and "Russet Burbank" was performed by the modified method described in De Block, *Theoret. Appl. Genet.* 76:767–774, 1988. Leaves (5 mm diameter) and stems from 4-week-old shoots were cut and further wounded with a sterile pipette tip. Approximately 15 wounded leaves and stems were floated upside down on 15 mL of "infection medium S2" (Murashige-Skoog (MS) medium (Murashige and Skoog, *Physiol. Plant.* 15:473–479, 1962) supplemented with 30 g/L sucrose, 0.5 g/L MES (2-[N-morpholino]ethanesulfonic acid pH 5.5), and 20 g/L mannitol) contained in a 9-cm diameter Petri dish. To each Petri dish, 60 μL of *Agrobacterium* bearing the plasmid pSAI4 (grown in LB with appropriate antibiotics to late log phase) were added. After incubation at low light intensity (500 lux) for 3 days, the leaves were washed with S2 medium containing 1 g/L carbenicillin, patted dry on sterile filter paper, placed upside down on medium S4 (Murashige-Skoog medium supplemented with 200 mg/L glutamine, 0.5 g/L MES pH 5.5, 0.5 g/L PVP, 20 g/L mannitol, 20 g/L glucose, 40 mg/L adenine-$SO_4$, 5 g/L agarose, 1 mg/L trans-zeatin, 0.1 mg/L naphthaline acetic acid (NAA), 1 g/L carbenicillin, 50 mg/L kanamycin, and 10 g/L $AgNO_3$), and incubated at room temperature at high light intensity (3,000 lux). After two weeks, many small calli had formed at the wounded edges of leaves and stems. The calli were transferred to fresh S6 medium (S4 medium without NAA). After another two weeks the calli were transferred to S8 medium (S6 medium plus 0.1 mg/mL gibberellin ($GA_3$)) to allow for shoot formation. After two additional weeks, the first shoots (0.5 cm long) could be transferred to S1 medium ("B5" medium, Gamborg et al., *Exp. Cell Res.* 50:151–158, 1968, with 20 g/L sucrose supplemented with 150 mg/L $CaCl_2$, 4 g/L agarose, pH 5.8, containing 1 g/L carbenicillin and 50 mg/L kanamycin) in Magenta jars. Normally, after one week the shoots were rooted. The regenerated plants were transferred to MS medium with 1 g/L carbenicillin, 50 mg/L kanamycin, and used for further analysis.

4. Screening of Calli for Disease Resistance

A simplified early detection method for disease-resistance assays was developed. Control and transgenic calli were grown on S4 medium (MS media without sucrose and supplemented with 200 mg/L glutamine, 0.5 g/L MES, pH 5.7, 0.5 g/L PVP, 20 g/L mannitol, 20 g/L glucose, 40 mg/L adenine-$SO_4$, 0.5% agarose, 1 mg/L trans-zeatin, 0.1 mg/L NAA, 1 g/L carbenicillin, and 50 µg/mL kanamycin, and 10 mg/L $AgNO_3$). The samples were then placed at room temperature at 3000 lux illumination to allow for callus formation. After two weeks, many small calli formed at wounded edges of the leaves and stems. The small calli were removed and transferred to fresh S6 medium (S4 without NAA). After 2–3 weeks, the calli were transferred to fresh medium and grown in the presence of phytopathogens (*Fusarium* or *Phytophthora*). Calli that survived and remained bright green were scored. No fungus-resistant calli were found in the control samples, and calli that were resistant to the fungal pathogen were found to be transformed.

5. Molecular Characterization of Transgenic Plants

DNA was isolated from transgenic potato and tobacco plants using the methods described below. In some instances purification involved a more rigorous protocol; in other instances a simple crude extract procedure was performed. In the more rigorous extract procedure, ten grams of fresh leaf tissue were obtained, and immediately frozen in liquid nitrogen. The frozen tissue was ground into a fine power and extracted with 20 mL extraction buffer (50 mM Tris-HCl buffer, 5 mM EDTA, 0.35 M sorbitol, 0.1% BSA, 0.1% P-mercaptoethanol, 10% polyetheylene glycol 4000). The homogenate was filtered through several layers of cheesecloth and one layer of Miracloth™ (Calbiochem, la Jolla, Calif., USA). The final purification steps were then performed in accordance with Wagner et al., *Proc. Natl. Acad. Sci. U.S.A.* 84:2097–2100, 1987.

The crude-extract procedure was used mainly to prepare a sample for PCR analysis. For this procedure, about 200 mg of fresh leaves were collected and ground in liquid nitrogen into a powder. 100 µL of 0.5 N NaOH were added to the powder and mixed (vortexed) for 30 seconds. The suspension was centrifuged for 5 minutes, and 5 µL of the supernatant was added to 45 µL of 100 mM Tris buffer (pH 8.0). The resulting crude genomic DNA extract was used as a template for PCR amplification.

Detection of the presence or absence of the ECEMA or CEMA construct was achieved by performing a PCR reaction using the extracted genomic DNA and the PCR primers shown in SEQ ID NOS: 9 and 10. According to this method, transgenic tobacco and potato plants transformed with the pDECEMA or pRSHECEMA constructs were identified.

In some cases, active expression of the transgene was confirmed by Northern blot analysis. The RNA substrate for such analyses was isolated and purified from the transgenic tobacco and potato plants. The protocol used for this isolation was performed in accordance with Verwoerd et al., *Nucl. Acids Res.* 17:2362, 1989.

In an illustrative example pDECEMA was used to transform potato cultivars. Two cultivars of potato, Russet Burbank and Desiree, were transformed with pDECEMA via *Agrobacterium tumefaciens*-mediated transformation. After antibiotic selection, kanamycin-resistant plants were regenerated. The integration of ECEMA (SEQ ID NO: 4) into plant genomic DNA was confirmed by PCR amplification of the ECEMA sequence (SEQ ID NO: 3) from genomic DNA isolated from non-transformed (control), and transgenic plants. The size of the amplified DNA fragment was the same as the fragment amplified from pDECEMA plasmid DNA. Similarly, in Desiree, transgenic plants a band was detected in PCR products of genomic DNA of transformed plants but not in non-transformed plants. Thus, ECEMA (SEQ ID NO: 4) had been successfully integrated into the genome of these transgenic potato plants.

The expression of ECEMA (SEQ ID NO: 4) was tested at the RNA level using RT-PCR. Expression was confirmed in all transgenic lines of Russet Burbank, and Desiree cultivars, while no RNA product appeared from the control plants. Furthermore, the lack of bands in RNA samples that were treated with DNAse prior to PCR proved that the RNA samples were not contaminated by genomic DNA (FIG. 2).

Figures 3A, 3B, 3C, 3D, 3E, 3F:
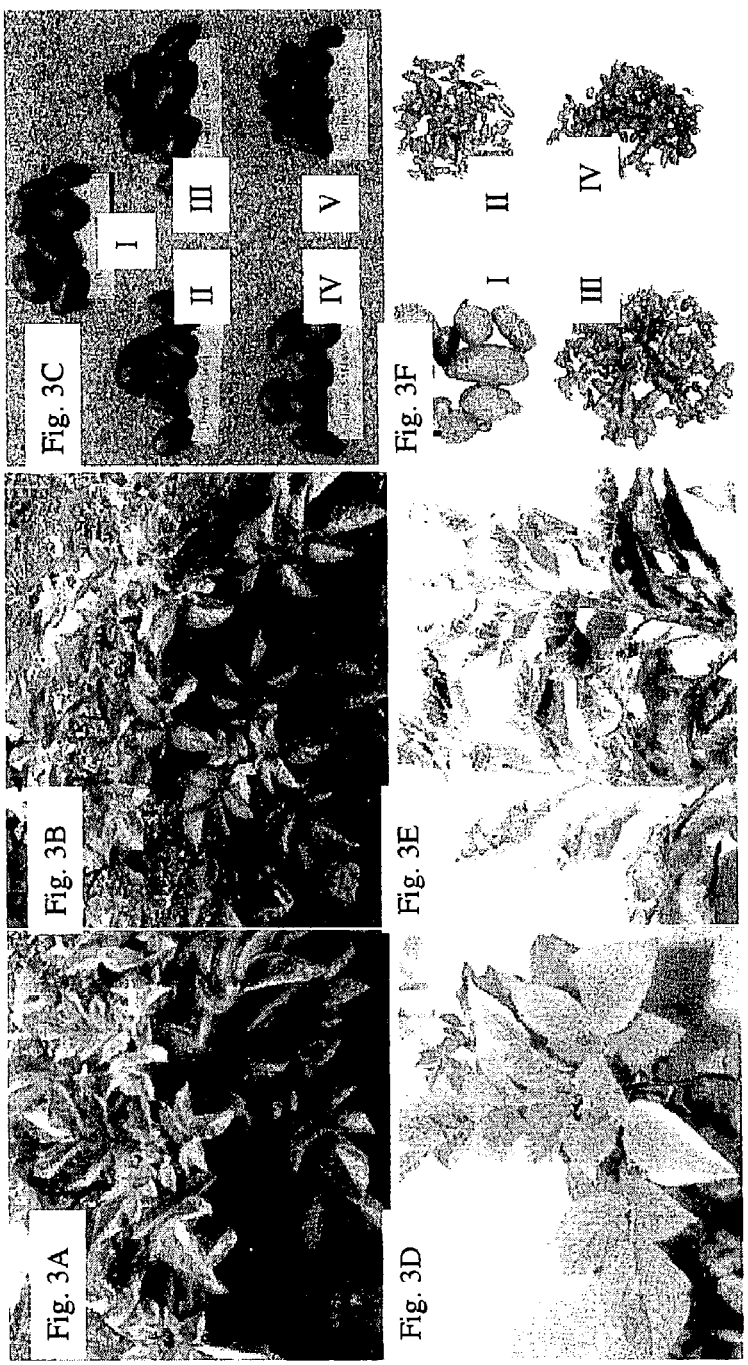
FIGS. 3A–3F include digital images showing the morphological characteristics of transgenic potato plants and tubers. Desiree control (FIG. 3A) and ECEMA transgenic plants (FIG. 3B) were photographed after transfer to soil in the greenhouse. Tubers from control (FIG. 3, C I) and transgenic (FIG. 3, C II, III, IV, V) plants were photographed after harvesting. Russet Burbank control (FIG. 3D) and ECEMA transgenic plants (FIG. 3E) were photographed after transfer to soil. Tubers from control (FIG. 3, F I) and transgenic (FIG. 3, F II, III, IV) plants were photographed after harvesting.
Figures 5A, 5B, 5C:
FIGS. 5A–5C are digital images showing a transgenic control plant (2X35S GUS.
Figure 7A:
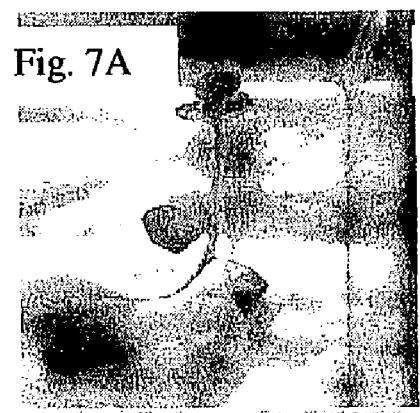
FIGS. 7A–7D are digital images of respective transgenic potato plants challenged with a fungal pathogen *Fusarium solani*. After rooting in MS medium, the control (FIG. 7A) and ECEMA transgenic (FIG. 7B) Russet Burbank plants, and the control (FIG. 7C) and ECEM transgenic (FIG. 7D) Desiree plants were challenged with *Fusarium solani*. Pictures were taken 11 days (FIGS. 7A and 7B) or 19 days (FIGS. 7C and 7D) after infection. The control plants were heavily infected while the transgenic plants were still green and growing.
Figure 7B:
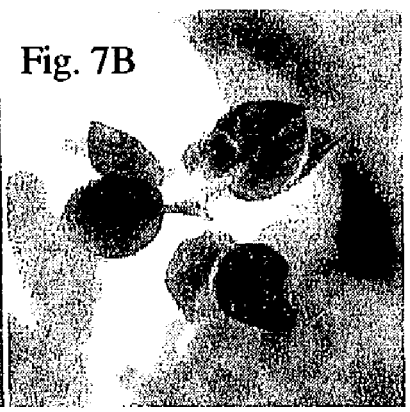
Figure 7C:
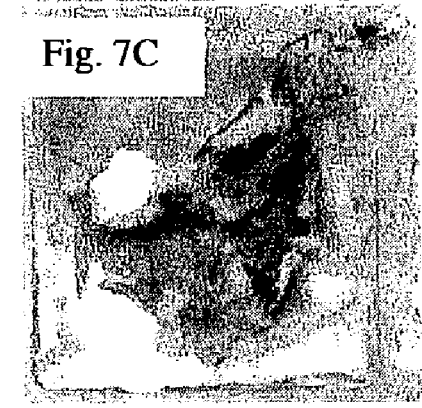
Figure 7D:
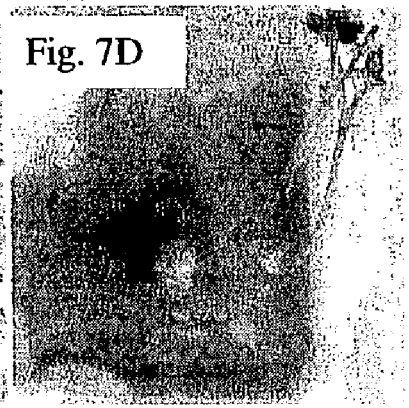

The morphological characteristics of transgenic Desiree plants and tubers expressing ECEMA (SEQ ID NO: 4) were comparable to that of control non-transformed plants (FIGS. 3A–3B). However, the expression of ECEMA (SEQ ID NO:4) in Russett Burbank caused morphological changes in transgenic potato plants when compared to the control plant. The most striking changes were observed on leaves that became curly, and on tubers that were much smaller and branched. This apparent "lesion-mimic" phenotype was observed in all Russet Burbank transgenic lines tested (FIGS. 3D–3F).

Despite the "lesion-mimic," the yield (total tuber mass/plant) of the Russet Burbank ECEMA-expressing transgenic plants was equivalent to the yield of the control non-transformed plant.

The yield (total tuber mass/plant) of the ECEMA expressing Desiree plants (1,845 g) was greater than that of the control plant transformed with GUS (1,544 g), and the non-transformed control (1,502 g).

Additionally, in a series of control experiments transgenic plants expressing either GUS, Douglas fir NADPH-cytochrome P450 reductase, or pProCEMA, were selected in a similar fashion to the above constructs. None of these transgenic plants exhibited the disease-resistance trait.

6. Resistance to Bacterial Pathogens

To examine the resistance of transgenic potato plants to the bacterial pathogen *Erwinia carotovora* cv *carotovora*, 2 mL of an overnight culture of the pathogen (grown in LB medium at room temperature) were diluted 5-fold with sterile distilled $H_2O$. One mL of this diluted culture was added to 2 mL liquid MS medium in test tubes. Freshly cut branches (4 cm long) from transgenic or control potato plants were inserted into the test tubes with the bottom edge of each branch immersed into bacterial culture and incubated at room temperature.

Results showed that, after one week, the control plants were seriously infected, and growth inhibited. Subsequently, the plants died. In contrast, the transgenic plants were unaffected and continued to grow, demonstrating that expression of ECEMA increased the resistance of potato plants to this bacterial pathogen.

Tubers harvested from "Desiree" plants expressing CEMA and ECEMA (as well as control plants) were also tested for tuber-tissue resistance to *E. carotovora*. For qualitative tests, 20 µL of 100× diluted overnight bacterial culture (approximately 2×10$^7$ CFU) were pipetted onto the surface of discs (2 cm diameter, 1 cm thick) prepared from tubers using a sterile cork borer. Tuber discs were then incubated in Petri dishes at room temperature for 6 days. For quantitative tests, a small well was made into each of the tuber discs (2 cm diameter, 3 cm thick). Twenty microliters of 100× diluted overnight bacterial culture were pipetted into each well and the discs were incubated at room temperature for 6 days. Afterward, any rotted tissue was gently removed from the tuber discs, and the mass of the remaining tissue determined.

Results showed that, after six days of incubation with 2×10$^7$ CFU of *E. carotovora*, the control (C; FIG. 4A) potato tubers had lost approximately 60% of their fresh weight primarily due to soft rot. The loss of weight of tuber discs which originated from transgenic Desiree plants (ME1, ME2, ME3; FIG. 4A) infected with *E. carotovora* was <5% and comparable to non-infected discs (FIG. 4A). In another experiment, the discs from control (non-transformed) potato had largely decomposed, while the discs from ECEMA-expressing plants were unaffected. After six months of storage at 4° C., approximately one-third of tubers from non-transformed potato were naturally infected and spoiled, and all ECEMA-expressing transgenic lines remained healthy with no sign of disease.

7. Resistance to Fungi

Mature plants were tested for their resistance to various fungi using the following protocol. Slices (1 cm×1 cm×0.5 cm) of medium containing *Fusarium* or *Phytophthora* sp. were cut and placed in the center of fresh plates of V8 agar medium (250 mL/L V8 juice, 7 g/L agar) in a 9-cm petri dish and grown for about one month at room temperature, or until the fungal mycelia completely covered the petri dish. Shoots of transgenic plants (~10 cm) were cut and transferred into MS medium for further growth. According to different treatments, plants were allowed to grow for 3 days or 2 weeks until the shoots rooted. Two slices (1 cm×1 cm×0.5 cm) of the fungal agar were then applied to both sides of the plant shoots without wounding the shoots. The resulting degree of infection was then determined visually.

In a representative experiment, respective transgenic potato plants (Russet Burbank and Desiree) transformed with either pDECEMA or pProCEMA, tobacco plants transformed with pRSHECEMA, pDECEMA, or pProCEMA, and control potato and tobacco plants were exposed to *Phytophthora cactorum*. After 7 days, *Phytophthora cactorum* had grown over the surface of MS medium and penetrated into the roots and the stems of the control plants, causing impairment of vital plant functions. It was apparent that the roots in the control plants were severely damaged. The interaction between control plants and fungi caused the secretion of yellow-brown pigments indicative of decay. Subsequently, the control plants lost water and their leaves became curly, the bottoms of the respective stems softened, and the roots died. In contrast, the transgenic plants stayed healthy and exhibited no disease symptoms, even though the fungal mycelia completely covered the MS media.

In another experiment, a pDCEMA transgenic potato plant and a control potato plant transformed with pProCEMA were challenged with *Fusarium solani*. After 6 days, *Fusarium* grew all over the surface of MS medium. The damage to the roots of the control plants was severe. The base of the stem of the control plant was penetrated by *Fusarium*, the stems were softened, and the veins of infected leaves exhibited clear browning and necrosis. After several days, the control plant collapsed and died. However, the transgenic plant continued to grow even under the extreme fungal infestation by *Fusarium solani*.

A similar set of experiments was performed using the pDECEMA-transformed Russet Burbank and Desiree plants with the phytopathogenic fungus *Fusarium solani*. Six days post-infection, *Fusarium* had grown all over the surface of the MS medium, and the roots and stems of the control plants were severely damaged. Eleven days after infection, the control plant was dead, while the transgenic plants were still growing normally with no evidence of infection.

Expression of ECEMA strongly increased the resistance of the Russet Burbank and Desiree plants to bacterial (*Erwinia* sp.) as well as fungal (*Fusarium, Phytophthora* sp.) phytopathogens making ECEMA an extremely promising tool in plant antimicrobial warfare. These results have been duplicated in tobacco although without the lesion-mimic effect. The above-described protocol involved a highly stringent bioassay for disease resistance using co-cultivation with high levels of aggressive phytopathogens with survival as the end point, whereas others have relied on less stringent assays such as the enhanced resistance toward lesion formation as an indicator of infectivity (Cao et al., *Proc. Natl. Acad. Sci. USA* 95:6531–6536, 1999; and Heo et al., *Proc. Natl. Acad. Sci. USA* 96:766–771, 1999)

It is probable that the challenge model described above, where whole plants are grown in the presence of the pathogens, more closely represents a field situation where soil and infected plants provide a constant reservoir of phytopathogens. In this regard the transgenic plants described herein have been grown for more than two months in the presence of both bacterial and fungal pathogens with still no evidence of disease. Furthermore, the transgenic potato tubers produced here retain their antimicrobial characteristics for over a year in storage at 4° C. and remain resistant to *Erwinia* soft rot. The extraction of ECEMA described below has also allowed for an estimated concentration of ECEMA at approximately 3–4 µg/g of raw tuber tissue that is sufficient to protect the tubers from bacterial attack. Additionally, preliminary feeding trials for a month showed that the tubers from ECEMA-expressing transgenic potato plants were not toxic to mice.

Constitutive expression of ECEMA can also cause morphological changes, similar to the so-called "lesion-mimic" phenotype, as described above in the case of the transgenic Russet Burbank potato. This phenomenon has been observed, where the expression of foreign genes in plants can trigger the activation of plant-defense mechanisms normally activated only during pathogenesis in an attempt to curtail the pathogen. Mittler et al., *Trends Microbiol.* 4:10–15, 1996: Abad et al., *Mol Plant Microbe Interact.* 10:635–645, 1997; and Dempsey et al., *Trends Microbiol.* 6: 54–61, 1997. However, in these previously reported observations of transgenic plants that displayed the lesion-mimic response, the plants did not display broad-spectrum pathogen resistance. This is in contrast to the data reported here that show that the ECEMA-expressing Russet Burbank plants display high levels of antimicrobial activity even though these plants display the lesion mimic response. Therefore, it is believed that transgenic plants displaying the lesion mimic phenotype in response to the expression of the transgenes disclosed herein will maintain pathogen resistance.

8. Production of Biologically Active ECEMA 10 g of tissue from potato tuber were ground to a fine powder under liquid $N_2$ and extracted for 30 min at 4° C. with 10 mL of Extraction Buffer (EB; 50 mM Bicine-NaOH pH 9.0; 1 mM EDTA; 20 mM NaCl; 1% Triton X-100) containing a protease and phosphatase inhibitor cocktail (P 9599, Sigma). The homogenate was centrifuged for 30 min at 12,000 rpm (Beckman J2-21) at 4° C., and the supernatant filtered through a 0.45-μm filter to remove particulate material. The resulting homogenate was applied to the cation-exchange column HiTrap™ SP (0.7×2.5 cm; Pharmacia Biotech, Sweden) equilibrated with EB. After washing with 6 column volumes of EB containing protease inhibitors, bound proteins and peptides were eluted with stepwise gradient of NaCl (0.2 M, 0.3 M, and 0.5 M) in EB with protease inhibitors. The fractions were then analyzed on Tricine-SDS-polyacrylamide gels (Schagger et al., *Anal. Biochem.* 166:368–379, 1987), and used for in vitro antibacterial assays.

Using the extraction procedure described above, the presence of ECEMA was demonstrated in and partially purified from transgenic potato tubers. Furthermore, the bactericidal activity (with *E. carotovora* as a target) could be observed only in those fractions containing the peptide of the same size as ECEMA (FIG. 1B). Both the peptide and bactericidal activity were completely absent from control, non-transgenic tubers of the same age. These results confirmed that tubers from transgenic plants contained biologically active ECEMA in concentrations sufficient to retain their antibacterial properties during prolonged storage at 4° C.

9. Transformed Plants and Tubers are Resistant to Late Blight (*P. infestans* Isolates US-8 and US-11)

Two strains of *Phytophthora infestans* (US-11 A1 and US-8 A1) were cultured on rye agar. The rye agar was prepared by boiling 120 g of organically grown rye kernels in 2 L of distilled water. The water was then allowed to boil down to 1000–1250 mL. The resulting mixture was then strained through a strainer on cheesecloth to remove kernels. The collected supernatant was then centrifuged at 2000 rpm for 5 minutes and then the volume was brought up to 2 L with distilled water. Two g of dextrose and 27 g BactoAgar™ was added and the media was autoclaved (121° C. for 40 minutes), and then cooled and poured.

For inoculation of plants the two strains were diluted in water to create a sporangial suspension of late blight containing 5,000–10,000 sporangia/mL that was chilled at 5° C. to produce zoospores. The resulting sporangia containing mixture was sprayed on 5 standard potato lines with known late blight resistance and the ECEMA-transgenic Desiree plants. The plants were grown in a plastic tent and mist was introduced to promote disease establishment.

Foliar ratings were conducted 7, 14, and 21 days post inoculation to assess the percent defoliation due to late blight. The results showed that the transgenic potato plants (Desiree) were more resistant to late blight than any of the five control lines tested (FIG. 5).

Similar experiments were conducted to assess the resistance to transgenic tubers (Desiree) to late blight. Fifteen to twenty tubers of each potato clone were washed before inoculation to remove soil from the tuber surface and to select those without disease symptoms. Replicate tubers of each potato clone were dip-inoculated in a sporangial suspension of late blight for each of the US-8 and US-11 genotypes. The study also included five potato lines known to be blight-resistant. The inoculated tubers were incubated in a sealed climate-controlled chamber for 14–21 days at 12° C. and 95–100% humidity. The results indicated that the transgenic tubers were more resistant to late blight than any of the five control lines tested.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

The invention claimed is:

1. A transgenic plant, wherein the plant expresses a cationic peptide comprising SEQ ID NO: 2.

2. The transgenic plant of claim 1, wherein the transgenic plant is a potato, tobacco, maize, wheat, rice, barley, soybean, legume, rape/canola, alfalfa, flax, sunflower, safflower, brassica, cotton, flax, peanut, clover, cucurbits, cassava, pea, lentil, vegetable, citrus tree, fruit tree, flower, cacao, coffee, rubber tree, conifer, deciduous tree, or grass.

3. The transgenic plant of claim 1, wherein the transgenic plant is a potato plant.

4. The transgenic plant of claim 1, wherein the transgenic plant is a tobacco plant.

5. A method of generating at least one cationic peptide, the method comprising:
propagating the transgenic plant of claim 1; and
isolating the cationic peptide from the transgenic plant or from a part of the transgenic plant.

6. A method for generating at least part of a plant with increased shelf-life or storage life, the method comprising:
growing the transgenic plant of claim 1; and
harvesting at least a part of the plant, thereby generating a harvested plant part, wherein the harvested plant part remains free from pathogen infection longer than a non-transgenic control.

7. The method of claim 6, wherein the plant part is a flower, a fruit or a vegetable.

8. A chimeric plant, comprising a first part and a second part, wherein the first part comprises tissue from the transgenic plant of claim 1, and the second part comprises non-transgenic plant tissue.

9. The transgenic plant of claim 1, wherein the cationic peptide comprising SEQ ID NO: 2 further comprises an N-terminal extension, wherein the N-terminal extension comprises SEQ ID NO: 5, 6, 7, 8 or 11.

10. The transgenic plant of claim 9, wherein the N-terminal extension comprises SEQ ID NO: 11.

11. The transgenic plant of claim 10, wherein the cationic peptide comprises SEQ ID NO: 4.

12. The transgenic plant of claim 1, wherein the cationic peptide comprising SEQ ID NO: 2 is expressed from a promoter regulated by wounding.

13. The transgenic plant of claim 12, wherein the transgenic plant is a tobacco plant.

14. A transgenic plant comprising a nucleic acid molecule encoding a peptide comprising an amino acid sequence selected from the group consisting of:
    (a) SEQ ID NO:2;
    (b) SEQ ID NO:4; and
    (c) amino acid sequences that share at least 95% sequence identity with SEQ ID NO:2 or SEQ ID NO:4, wherein the peptide has CEMA and CEMA-related peptide biological activity.

15. The transgenic plant of claim 14, wherein the transgenic plant is a potato, tobacco, maize, wheat, rice, barley, soybean, legume, rape/canola, alfalfa, flax, sunflower, safflower, brassica, cotton, flax, peanut, clover, cucurbits, cassava, pea, lentil, vegetable, citrus tree, fruit tree, flower, cacao, coffee, rubber tree, conifer, deciduous tree, or grass.

16. The transgenic plant of claim 15, wherein the transgenic plant is a potato plant.

17. The transgenic plant of claim 15, wherein the transgenic plant is a tobacco plant.

18. A method of generating at least one cationic peptide, the method comprising:
    propagating the transgenic plant of claim 14; and
    isolating the cationic peptide from the transgenic plant or from a part of the transgenic plant.

19. A method for generating at least part of a plant with increased shelf-life or storage life, the method comprising:
    (a) growing the transgenic plant of claim 14; and
    (b) harvesting at least a part of the plant, thereby generating a harvested plant part, wherein the harvested plant part remains free from pathogen infection longer than a non-transgenic control.

20. The method of claim 19, wherein the plant part is a flower, a fruit or a vegetable.

21. A chimeric plant, comprising a first part and a second part, wherein the first part comprises tissue from the transgenic plant of claim 14, and the second part comprises non-transgenic plant tissue.

22. The transgenic plant of claim 14, wherein the transgenic plant displays an increased yield of plants or plant products when compared to its non-transgenic counterpart.

23. A transgenic plant, according to claim 14, wherein the transgenic plant displays resistance to late blight due to *Phytophthora infestans*.

24. The transgenic plant of claim 14, wherein the transgenic plant displays resistance to soft rot due to *Erwinia carotovara*.

25. The transgenic plant of claim 14, wherein the peptide further comprises an anionic pro-region peptide operably linked to an N-terminus of the peptide.

26. The transgenic plant of claim 14, wherein the peptide further comprises an N-terminal extension.

27. The transgenic plant of claim 26, wherein the N-terminal extension is joined to the cationic peptide by a spacer peptide.

28. The transgenic plant of claim 26, wherein the N-terminal extension modulates an anti-microbial activity of the cationic peptide.

29. The transgenic plant of claim 26, wherein the N-terminal extension comprises an amino acid sequence no more than 25 amino acid residues long.

30. The transgenic plant of claim 26, wherein the N-terminal extension comprises an anionic pro-region peptide.

31. The transgenic plant of claim 30, wherein the anionic pro-region peptide is operably linked at the N-terminus of the N-terminal extension.

32. The transgenic plant of claim 30, wherein the anionic pro-region peptide is operably linked to the N-terminus of SEQ ID NO: 11.

33. The transgenic plant of claim 26, wherein the N-terminal extension comprises SEQ ID NO: 5, 6, 7, or 8.

34. The transgenic plant of claim 14, wherein the peptide further comprises an C-terminal extension.

35. A transgenic plant, comprising a recombinant nucleic acid molecule encoding a peptide comprising the amino acid sequence of SEQ ID NO: 4.

36. A transgenic plant according to claim 35, wherein the transgenic plant is a potato, tobacco, maize, wheat, rice, barley, soybean, legume, rape/canola, alfalfa, flax, sunflower, safflower, brassica, cotton, flax, peanut, clover, cucurbits, cassava, pea, lentil, vegetable, citrus tree, fruit tree, flower, cacao, coffee, rubber tree, conifer, deciduous tree, or grass.

37. The transgenic plant of claim 35, wherein the transgenic plant is a potato plant.

38. The transgenic plant of claim 35, wherein the transgenic plant is a tobacco plant.

39. A method of generating at least one cationic peptide, the method comprising: propagating the transgenic plant of claim 35; and
    isolating the cationic peptide from the transgenic plant or from a part of the transgenic plant.

40. A method for generating at least part of a plant with increased shelf-life or storage life, the method comprising:
    (a) growing the transgenic plant of claim 35; and
    (b) harvesting at least a part of the plant, thereby generating a harvested plant part, wherein the harvested plant part remains free from pathogen infection longer than a non-transgenic control.

41. The method of claim 40, wherein the plant part is a flower, a fruit or a vegetable.

42. A chimeric plant, comprising a first part and a second part, wherein the first part comprises tissue from the transgenic plant of claim 35, and the second part comprises non-transgenic plant tissue.

43. A method for producing a transgenic plant that expresses a terminally extended cationic peptide conferring broad-spectrum pathogen resistance and that is compatible with plant physiology, the method comprising:
    (a) transforming a plant cell with a nucleic acid sequence that encodes a cationic peptide, wherein the cationic peptide comprises SEQ ID NO:2 operably linked to an N-terminal extension; and
    (b) expressing the cationic peptide in a plant, wherein such expression confers broad-spectrum pathogen resistance to the plant.

44. The method of claim 43, wherein the N-terminal extension is selected from the group consisting of SEQ ID NOS: 5, 6, 7, 8, and 11.

45. A transgenic plant, produced by the method of claim 43.

46. A transgenic plant according to claim 45, wherein the transgenic plant is a potato, tobacco, maize, wheat, rice, barley, soybean, legume, rape/canola, alfalfa, flax, sunflower, safflower, brassica, cotton, flax, peanut, clover, cucurbits, cassava, pea, lentil, vegetable, citrus tree, fruit tree, flower, cacao, coffee, rubber tree, conifer, deciduous tree, or grass.

47. The transgenic plant of claim 45, wherein the transgenic plant is a potato plant.

48. The transgenic plant of claim 45, wherein the transgenic plant is a tobacco plant.

49. A method of generating at least one cationic peptide, the method comprising: propagating-the transgenic plant of claim 45; and
isolating the cationic peptide from the transgenic plant or from a part of the transgenic plant.

50. A method for generating at least part of a plant with increased shelf-life or storage life, the method comprising:
growing a transgenic plant of claim 45; and
harvesting at least a part of the plant, thereby generating a harvested plant part, wherein the harvested plant part remains free from pathogen infection longer than a non-transgenic control.

51. The method of claim 50, wherein the plant part is a flower, a fruit or a vegetable.

52. A chimeric plant, comprising a first part and a second part, wherein the first part comprises tissue from the transgenic plant of claim 45, and the second part comprises non-transgenic plant tissue.

53. The transgenic plant of claim 45, wherein the transgenic plant displays an increased yield of plants or plant products when compared to its non-transgenic counterpart.

54. The transgenic plant of claim 45, wherein the transgenic plant displays resistance to late blight due to *Phytophthora infestans*.

55. The transgenic plant of claim 45, wherein the transgenic plant displays resistance to soft rot due to *Erwinia carotovara*.

* * * * *

UNITED STATES PATENT AND TRADEMARK OFFICE
CERTIFICATE OF CORRECTION

| | |
|---|---|
| PATENT NO. | : 7,105,725 B2 |
| APPLICATION NO. | : 10/421635 |
| DATED | : September 12, 2006 |
| INVENTOR(S) | : Misra et al. |

It is certified that error appears in the above-identified patent and that said Letters Patent is hereby corrected as shown below:

Column 7, line 63, "$10^{4-105}$" should be --$10^4 - 10^5$--.

Column 9, line 47, "*CABIOS*5:151–153" should be --*CABIOS* 5:151–153--.

Column 19, line 48, "pSAII" should be --pSAI1--.

Column 21, line 44, "P-mercaptoethanol" should be --$\beta$-mercaptoethanol--.

Column 26, line 5-6, "BactoA-gar$^{TM}$" should be --BactoAgar$^{TM}$--

Signed and Sealed this

First Day of May, 2007

JON W. DUDAS
*Director of the United States Patent and Trademark Office*